US00RE38532E

(19) United States
(12) Reissued Patent
Heyse et al.

(10) Patent Number: US RE38,532 E
(45) **Date of Reissued Patent: *Jun. 8, 2004**

(54) HYDRODEALKYLATION PROCESSES

(75) Inventors: John V. Heyse, Crockett, CA (US); Bernard F. Mulaskey, Fairfax, CA (US); Robert A. Innes, San Rafael, CA (US); Daniel P. Hagewiesche, Oakland, CA (US); William J. Cannella, Hercules, CA (US); David C. Kramer, San Anselmo, CA (US)

(73) Assignee: Chevron Phillips Chemical Company LP, The Woodlands, TX (US)

( * ) Notice: This patent is subject to a terminal disclaimer.

(21) Appl. No.: 09/455,515

(22) Filed: Dec. 6, 1999

Related U.S. Patent Documents

Reissue of:
(64) Patent No.: 5,866,743
Issued: Feb. 2, 1999
Appl. No.: 08/584,159
Filed: Jan. 11, 1996

U.S. Applications:
(63) Continuation of application No. 08/177,126, filed on Jan. 4, 1994, now abandoned, which is a continuation-in-part of application No. 08/000,017, filed on Jan. 4, 1993, now abandoned.

(51) Int. Cl.[7] ..... C07C 4/12

(52) U.S. Cl. ..... 585/486; 585/483; 585/485; 585/488; 585/950; 518/700; 518/728; 423/650; 423/651

(58) Field of Search ..... 585/483, 485, 585/486, 488, 950; 518/700, 728; 423/650, 651

(56) References Cited

U.S. PATENT DOCUMENTS

| | | | |
|---|---|---|---|
| 1,883,630 | A | 10/1932 | Duff |
| 2,063,596 | A | 12/1936 | Feiler |
| 2,263,366 | A | 11/1941 | Peck et al. |
| 2,818,374 | A | 12/1957 | Certa et al. |
| 2,929,775 | A | 3/1960 | Aristoff et al. |
| 3,160,671 | A | 12/1964 | Feigelman et al. |
| 3,169,000 | A | 2/1965 | Ernst et al. |
| 3,178,321 | A | 4/1965 | Satterfield |
| 3,284,526 | A | 11/1966 | Frayer et al. |
| 3,459,821 | A | 8/1969 | Englebrecht et al. |
| 3,531,394 | A | 9/1970 | Koszman |
| 3,531,543 | A | 9/1970 | Clippinger et al. |
| 3,536,776 | A | 10/1970 | Lo |
| 3,584,060 | A | 6/1971 | Rausch |
| 3,607,960 | A | 9/1971 | Button et al. |
| 3,617,359 | A | 11/1971 | Wakefield |
| 3,631,215 | A | 12/1971 | Clippinger et al. |
| 3,686,340 | A | 8/1972 | Patrick et al. |
| 3,700,745 | A | 10/1972 | Kovach et al. |
| 3,767,456 | A | 10/1973 | Glaski |
| 3,827,967 | A | 8/1974 | Nap et al. |
| 3,835,183 | A | 9/1974 | Carpenter et al. |
| 3,864,284 | A | 2/1975 | Clippinger et al. |
| 3,878,131 | A | 4/1975 | Hayes |
| 3,890,110 | A | 6/1975 | Glaski |
| 3,890,686 | A | 6/1975 | Caubet |
| 3,919,073 | A | 11/1975 | Bagnoli et al. |
| 3,955,935 | A | 5/1976 | Shockley et al. |
| 3,966,833 | A | 6/1976 | Cosyns et al. |
| 4,013,487 | A | 3/1977 | Ramqvist et al. |
| 4,015,950 | A | 4/1977 | Galland et al. |
| 4,019,969 | A | 4/1977 | Golebiowski et al. |
| 4,058,452 | A | 11/1977 | Loboda |
| 4,111,763 | A | 9/1978 | Pryor |
| 4,132,743 | A | 1/1979 | Castor et al. |
| 4,161,510 | A | 7/1979 | Eldridge |
| 4,163,706 | A | 8/1979 | Horowitz et al. |
| 4,167,532 | A | 9/1979 | Walker et al. |
| 4,167,533 | A | 9/1979 | Raymond |
| 4,173,457 | A | 11/1979 | Smith |
| 4,179,361 | A | 12/1979 | Michlmayr |
| 4,189,613 | A | 2/1980 | Bjornson |
| 4,191,632 | A | 3/1980 | Cosyns et al. |
| 4,191,846 | A | 3/1980 | Farha, Jr. et al. |
| 4,204,997 | A | 5/1980 | Hobbs et al. |
| 4,208,302 | A | 6/1980 | McKay |

(List continued on next page.)

FOREIGN PATENT DOCUMENTS

| | | | |
|---|---|---|---|
| DE | 1521848 | * | 4/1969 |
| EP | 0 082 920 | | 7/1983 |
| EP | 0 146 081 | | 6/1985 |
| EP | 0 192 059 | | 8/1986 |
| EP | 0 351 067 | | 1/1990 |
| EP | 0 403 976 | | 12/1990 |
| GB | 0 313 303 | | 8/1929 |
| GB | 0 317 303 | | 8/1929 |
| GB | 1 054 121 | | 1/1967 |
| GB | 1 122 017 | | 7/1968 |
| GB | 1 149 163 | | 4/1969 |
| GB | 2 066 696 | | 7/1981 |
| GB | 1 604 604 | | 12/1981 |
| GB | 2 162 082 | | 1/1986 |
| GB | 2 234 530 | | 2/1991 |
| WO | WO92/15653 | | 9/1992 |
| WO | WO94/15896 | | 7/1994 |

OTHER PUBLICATIONS

"Report of the Panel on High Temperature Carburization to the Subcommittee on Corrosion", May 1963 (unclear whether a publication).

Robert Schueler, Hydrocarbon Processing, Aug. 1972.

R. Hochman and J. Burson III, Proceedings Division of Refining, "The Fundamentals of Metal Dusting", vol. 46 (1966).

G. L. Swales, "High Temperature Corrosion Problems in the Petroleum Refining and Petrochemical Industries", pp. 45–82 (no date).

(List continued on next page.)

*Primary Examiner*—Walter D. Griffin
(74) *Attorney, Agent, or Firm*—Pennie & Edmonds LLP

(57) ABSTRACT

Carburization and metal-dusting while hydrodealkylating a hydrodealkylatable hydrocarbon are reduced even in the substantial absence of added sulfur.

144 Claims, 1 Drawing Sheet

U.S. PATENT DOCUMENTS

| | | | | | |
|---|---|---|---|---|---|
| 4,215,231 | A | | 7/1980 | Raymond | |
| 4,264,433 | A | | 4/1981 | McKay | |
| 4,268,188 | A | | 5/1981 | Bertus et al. | |
| 4,271,008 | A | | 6/1981 | Vogt et al. | |
| 4,297,150 | A | | 10/1981 | Foster et al. | |
| 4,350,719 | A | | 9/1982 | Baldi | |
| 4,385,645 | A | | 5/1983 | Campbell et al. | |
| 4,404,087 | A | | 9/1983 | Reed et al. | |
| 4,410,418 | A | | 10/1983 | Kukes et al. | |
| 4,438,288 | A | | 3/1984 | Imai et al. | |
| 4,447,316 | A | | 5/1984 | Buss | |
| 4,451,687 | A | | 5/1984 | Daly et al. | |
| 4,456,527 | A | | 6/1984 | Buss et al. | |
| 4,463,206 | A | | 7/1984 | Derrien et al. | |
| 4,467,016 | A | | 8/1984 | Baldi | |
| 4,471,151 | A | | 9/1984 | Kolts | |
| 4,488,578 | A | | 12/1984 | Tseung et al. | |
| 4,507,196 | A | | 3/1985 | Reed et al. | |
| 4,511,405 | A | | 4/1985 | Reed et al. | |
| 4,545,893 | A | | 10/1985 | Porter et al. | |
| 4,551,227 | A | | 11/1985 | Porter et al. | |
| 4,552,643 | A | | 11/1985 | Porter et al. | |
| 4,555,326 | A | | 11/1985 | Reid | |
| 4,595,673 | A | | 6/1986 | Imai et al. | |
| 4,613,372 | A | | 9/1986 | Porter et al. | |
| 4,665,267 | A | | 5/1987 | Barri | |
| 4,666,583 | A | | 5/1987 | Porter et al. | |
| 4,685,427 | A | | 8/1987 | Tassen et al. | |
| 4,686,201 | A | | 8/1987 | Porter et al. | |
| 4,687,567 | A | | 8/1987 | Porter et al. | |
| 4,692,234 | A | | 9/1987 | Porter et al. | |
| 4,716,143 | A | | 12/1987 | Imai | |
| 4,727,216 | A | | 2/1988 | Miller | |
| 4,741,819 | A | | 5/1988 | Robinson et al. | |
| 4,743,318 | A | | 5/1988 | Fischer et al. | |
| 4,762,681 | A | | 8/1988 | Tassen et al. | |
| 4,786,625 | A | | 11/1988 | Imai et al. | |
| 4,795,732 | A | | 1/1989 | Barri | |
| 4,804,446 | A | | 2/1989 | Lashmore et al. | |
| 4,804,487 | A | | 2/1989 | Reed et al. | |
| 4,827,072 | A | | 5/1989 | Imai et al. | |
| 4,863,892 | A | | 9/1989 | Porter et al. | |
| 4,902,849 | A | | 2/1990 | McKay et al. | |
| 4,917,969 | A | | 4/1990 | Pircher et al. | |
| 4,925,549 | A | | 5/1990 | Robinson et al. | |
| 4,926,005 | A | | 5/1990 | Olbrich et al. | |
| 4,935,566 | A | | 6/1990 | Dessau et al. | |
| 4,976,932 | A | | 12/1990 | Maeda et al. | |
| 4,982,047 | A | | 1/1991 | Barri et al. | |
| 5,012,027 | A | | 4/1991 | Abrevaya et al. | |
| 5,015,358 | A | | 5/1991 | Reed et al. | |
| 5,053,574 | A | | 10/1991 | Tsutsui et al. | |
| 5,118,028 | A | | 6/1992 | Ogawa et al. | |
| 5,139,814 | A | | 8/1992 | Sugao | |
| 5,139,914 | A | | 8/1992 | Tomiyama et al. | |
| 5,238,492 | A | | 8/1993 | Itoh et al. | |
| 5,242,665 | A | | 9/1993 | Maeda et al. | |
| 5,405,525 | A | | 4/1995 | Heyse et al. | |
| 5,406,014 | A | | 4/1995 | Heyse et al. | |
| 5,413,700 | A | | 5/1995 | Heyse et al. | |
| 5,575,902 | A | | 11/1996 | Heyse et al. | |
| 5,593,571 | A | * | 1/1997 | Heyse et al. | 208/134 |
| 5,648,178 | A | * | 7/1997 | Heyse et al. | 428/627 |
| 5,658,452 | A | * | 8/1997 | Heyse et al. | 208/48 R |
| 5,674,376 | A | * | 10/1997 | Heyse et al. | 208/135 |
| 5,676,821 | A | * | 10/1997 | Heyse et al. | 208/135 |
| 5,723,707 | A | * | 3/1998 | Heyse et al. | 585/444 |
| 5,833,838 | A | * | 11/1998 | Heyse et al. | 208/48 R |
| 5,849,969 | A | * | 12/1998 | Heyse et al. | 585/483 |
| 5,863,418 | A | * | 1/1999 | Heyse et al. | 208/135 |
| 6,019,943 | A | * | 2/2000 | Buscemi et al. | 422/8 |

OTHER PUBLICATIONS

R. F. Hochman, "Catastrophic Deterioration of High Temperature Alloys in Carbonaceous Atmospheres", pp. 715–732, Proceedings of the Symposium on Properties of High Temperature Alloys, 1978.

Hettinger, Keith, Gring and leter, Industrial and Engineering Chemistry, "Hydroforming Reactions, Effect of Certain Catalyst Properties and Poisons", Apr. 1955.

F.A. Prange, Corrosion, "Corrosion in a Hydrocarbon Conversion System", vol. 15, Dec. 1959.

C.J. Polk, "Evaluating Catalytic Reformer Heating Tubing After Extended High–Temperature Service", Nat'l Assoc. of Corros. Engineers, Paper No. 50, Mar. 1980.

Excerpts from NPRA (National Petroleum Refiners Assoc.), Q&A, 1981 (Questions 17 & 21).

Excerpts from 1980 PEP Report, "Reforming for BTX". SRI International.

R.G. McClung, Oil & Gas Journal, pp. 98 & 99 (Oct. 1990).

D.M. Little, Catalytic Reforming, pp. 136–141. No Date.

Excerpts from NPRA, Q&A, 1982 (Question 21).

Buss et al, "New Developments in Rheniforming", 1978 NPRA Annual Meeting (1978).

Freiburger et al, "Recent Catalyst and Process Improvements in Commercial Rheniforming", 1980 NPRA Annual Meeting (1980).

King et al. "The Production of Ethylene by the Decomposition of n–Butane; the Prevention of Carbon Formation by the Use of Chromium Plating", Transactions of the E.I.C., vol. 3, No. 1, p. 1, (1959).

Platt's International Petrochemical Report (Oct. 1993).

J.R. Bernard, "Hydrocarbons Aromatization on Platium Alkaline Zeolites", Proceedings of the Fifth Int. Conf. Zeolites, pp. 686–695, Heydon, London (1980).

Shinohara, Kohchi, Shibata, Sugitani and Tsuchida; "Development of nondestructive technique for measuring carburization thickness and a new carburization—resistant allow"; Werkstoffe Und Korrosion, 1986; pp. 410–411.

Alon Processing, Inc.; "Alonized Steels for high temperature corrosion resistance"; 1990; pp. 1–19.

Micron, Inc. Analytical Service Laboratory; "Report #R–8126, Alonized Steel"; Jun. 1985.

W.A. McGill and M.J. Weinbaum, "The Selection, Application and Fabrication of Alonized Systems in the Refinery Environment"; 1975; pp. 1–18.

Pujado et al., "Make $C_3$–$C_4$ Olefins Selectively"; Hydrocarbon Processing; pp. 65–70; Mar. 1990.

Dunn, "HP In Construction"; Hydrocarbon Processing; pp. 41–42, Aug. 1991.

General Motor, "The Carbon Gradient" no date.

Pujado et al., "Production of LPG Olefins by Catalytic Dehydrogenation"; Energy Progress; vol. 4, No. 3; pp. 186–191; Sep. 1984.

Pujado et al., "OGJ Report"; Oil and Gas Journal; pp. 71–74; Mar. 1983.

Berg et al., "Catalytic LPG Dehydrogenation Fits in '80's Outlook"; Oil and Gas Journal; pp. 191–197; Nov. 1980.

Gussow et al., "Dehydrogenation Links LPG to More Octanges"; Oil and Gas Journal; pp. 96–101; Dec. 1980.

Tokyo Engineering Corp. and Kubota; "CORET, New Cracking Tube to Retard Coke Depositions"; Mar. 1986; pp. 1–5.

Tokyo Engineering Corp. and Kubota; "Development of Double–Layer Cast Tube for Anti–Carburization and the Retarding of Coke Deposition"; pp. 1–11, (No Date).

* cited by examiner

HYDRODEALKYLATION PROCESSES

Matter enclosed in heavy brackets [ ] appears in the original patent but forms no part of this reissue specification; matter printed in italics indicates the additions made by reissue.

This application is a continuation of application Ser. No. 08/177,126, filed Jan. 4, 1994, now abandoned, which is a continuation-in-part of application Ser. No. 08/000,017, filed Jan. 4, 1993, now abandoned.

BACKGROUND OF THE INVENTION

The present invention rotates to an improved technique for the hydrodealkylation of a hydrodealkylatable hydrocarbon, particularly under conditions of low sulfur, which minimizes carburization thus preventing premature plant shut-downs.

The hydrodealkylation of hydrodealkylatable hydrocarbons such as alkyl aromatics has been practiced for many years. The principal processes involve the conversion of toluene and like alkyl-substituted benzenes to benzene and various byproducts. Such processes are either catalytic or non-catalytic in nature. The catalytic processes employ one or more catalysis that promote the conversion of the alkyl aromatic compounds to benzene and the remaining alkyl. The non-catalytic processes typically employ heat and pressure to promote the conversion of the alkyl aromatic compounds to benzene and the remaining alkyl.

Some conventional catalytic hydrodealkylation processes employ Group VIII metals such as Rh and Pt supported on an alumina support. For example, Kovach et al., in U.S. Pat. No. 3,700,745, describes a hydrodealkylation process which includes contacting an alkyl aromatic hydrocarbon with a catalyst including an active Group VIII metal, such as, platinum, rhodium, palladium, ruthenium and nickel. Other catalytic hydrodealkylation processes employ chromia type catalysts deposited on an alumina support. For example, Daly et al., in U.S. Pat. No. 4,451,687, discloses a catalyst for the hydrodealkylation of alkylaromatic compounds containing chromia on an alumina support. Other catalytic hydrodealkylation processes employ variations of the above catalysts or even completely different catalysts. See, for example, U.S. Pat. Nos. 3,686,340, 3,966,833, 4,189,613, 4,191,632, 4,463,206 and 5,053,574.

The catalytic processes, however, are not always suitable for the commercial conversion of alkyl aromatic compounds to benzene and the remaining alkyl. In particular, the activity, selectivity and conversion rate of such catalysts are not always suitable for large scale hydrodealkylation at the temperatures and pressures suitably employed. If the reaction temperature or pressure is increased aide reactions such as hydrocracking of the aromatic ring is promoted.

Furthermore, some catalysts tend to deactivate with use, presumably due to coke formation on the catalyst surface. In this regard, it is believed that active sites promote polymerization of either hydrogenolysis products or aromatic hydrocarbons resulting in hydrocarbon condensation on the catalyst surface. Under the conditions of the process, these condensed species are dehydrogenated forming coke. The result of these reactions is a reduction in activity of the catalyst since the coke is strongly adsorbed onto the sites which promote dealkylation. In other words, this coke or carbon build-up either blocks or poisons the active catalyst sites casing deactivation. See U.S. Pat. No. 4,451,687.

Additionally, some catalysts tend to deactivate with use, due to the presence of sulfur and in particular thiophene sulfur in the process feed. Thus, catalysts such as certain noble metal catalysts deactivate over time due to the presence of sulfur in the feed. These catalysts must be replaced or regenerated when sulfur reduces the activation to an extent low enough to prevent suitable conversion of the feed.

In view of the disadvantages associated with utilizing catalytic hydrodealkylation processes, non-catalytic hydrodealkylation processes have been developed. Mainly, such processes employ the use of heat and pressure to convert alkylaromatic compounds to benzene and the disassociated alkyl compounds.

Button et al., in U.S. Pat. No. 3,607,960, and Loboda, in U.S. Pat. No. 4,058,452, disclose processes for the thermal hydrodealkylation of an alkyl aromatic, such as toluene, to produce benzene. Both processes include subjecting a gaseous mixture of at least one alkyl aromatic compound and hydrogen in a reaction zone to a reaction temperature in the range of about 1000° to 1800° F. and removing benzene from the effluent. Other patents which disclose the thermal dealkylation of hydrodealkylatable hydrocarbons include U.S. Pat. Nos. 2,929,775, 3,160,671, and 3,284,526.

Thermal hydrodealkylation processes ameliorate the disadvantages associated with the above-mentioned catalytic hydrodealkylation processes in that they do not employ the use of catalysts which are susceptible to deactivation. However, due to the use of high temperatures end pressures which are required for the conversion of alkyl aromatic compounds in the absence of a suitable catalyst, such processes have their own inherent problems.

SUMMARY OF THE INVENTION

With conventional hydrodealkylation techniques, added sulfur effectively inhibits carburization. Somehow, the sulfur interferes with the carburization reaction. But with low sulfur systems or with sulfur outages, this inherent protection no longer exists especially when the system is exposed to high temperatures such as in thermal hydrodealkylation.

The problems associated with carburization include coking, carburization of system metallurgy, and metal dusting. The embrittlement of the steel walls by carburization leads to "metal-dusting", i.e., a release of catalytically active particles and metal droplets of metal due to an erosion of the metal. The excessive "metal-dusting" adds active metal particulates to the system, which particulates provide additional sites for coke formation in the system.

Coking is generally not a problem which must be addressed in hydrodealkylation processes, but this significant source of calm formation due to the absence of sulfur in reactor feedstreams excessively aggravates the problem. In fact, active metal particulates in coke particles metastasize more generally throughout the system. That is, the active metal particulates actually induce coke formation on themselves and anywhere that the particles accumulate in the system resulting in coke plugs and hot regions of exothermic reactions. As a result, a premature coke-plugging of the reactor system occurs which can lead to a premature shut-down of the system.

One solution to the problem associated with carburization, embrittlement, and metal-dusting is to add sulfur to the feed to thereby effectively inhibit carburization. However, the addition of sulfur increases production cost and process complexity. Moreover, sulfur usage has inherent environmental and safety hazards which are preferably avoided. Moreover, at high temperatures coking and carburization will still occur even when sulfur is added to the feed.

Consequently, there remains a need in the art for improved processes for the hydrodealkylation of hydrodealkylatable compounds with reduced carburization, especially in the absence of, or at low levels of, sulfur. Such a method would include means for inhibiting the undesirable catalytic activity which causes carburization of system metal.

Accordingly, one object of the invention is to provide the technical background necessary for solutions to the problems associated with coking, carburization, and metal-dusting. In particular, the discovery of the mechanisms involved with carburization and metal-dusting which lead to premature coke-plugging allows those skilled in the art to formulate solutions to the problems.

Another object of this invention is to provide a method for inhibiting carburization and metal-dusting in a process for thermally dealkylating a hydrodealkylatable hydrocarbon. The process includes pretreating surfaces exposed to the dealkylation atmosphere to form a protective layer which is more resistant to embrittlement, carburization and metal-dusting than the materials conventionally used to manufacture the reactor system.

The use of the process of the present invention allows for the dealkylation of hydrodealkylatable hydrocarbons especially in the absence of sulfur. Thus, an advantage of the method for inhibiting carburization includes the lack of a need for the addition of sulfur to hydrocarbon feeds and any recycle streams. In addition, hydrocarbon foods having a low sulfur content may be used.

More preferably, the invention relates to a method for thermally hydrodealkylating hydrocarbons comprising contacting the hydrocarbons with hydrogen in a reactor system having as resistance to carburization and metal-dusting, which is an improvement over conventional steel reactor systems under conditions of low sulfur.

Another aspect of the invention includes providing a reactor system which prevents embrittlement. Preventing embrittlement significantly reduces metal-dusting and coking in the reactor system, and permits operation for longer periods of time. Furthermore, higher temperatures may be used during hydrodealkylation, especially in thermal hydrodealkylation processes, allowing for increased production.

Even another preferred embodiment relates to the discovery that simply providing a protective plating, cladding or other coating such as a paint, to a reactor system will not necessarily be sufficient to completely address the aforementioned problems. Such a protective layer must be of sufficient thickness to provide a complete, uninterrupted coating of the underlying base metal, and it must remain complete over time. Even minor imperfections, pinholes or other flaws in the protective layer an provide destructive carburization sites sufficient to shutdown operation.

An effective protective layer must resist deleterious chemical alteration, as well as peeling and/or splitting. Additionally, it has been found that any protective layer must be applied to a thickness sufficient to completely cover the surface to be protected, and must maintain its integrity through operation. As such, the protective layer must be sufficiently abrasion resistant during catalyst loading, start-up and operation.

According to this preferred embodiment them is used an intermediate bonding layer which anchors the protective layer to the steel substrate to be protected. In this regard, the reactor system comprises a steel portion having provided thereon a protective layer to isolate the steel portion from hydrocarbons, preferably a stannide layer, applied to a thickness effective for completely isolating the steel portion from the hydrocarbon environment, while avoiding any substantial liquid metal embrittlement. The protective layer is anchored to the steel substrate through an intermediate carbide-rich (relative to the underlying steel), bonding layer; in the case of a stainless steel substrate, an intermediate carbide-rich, nickel-depleted (relative to the underlying steel) bonding layer.

In the case of a stannide outer protective layer and a stainless steel substrate, the stannide layer is nickel-enriched and comprises carbide inclusions, while the intermediate carbide-rich, nickel-depleted bonding layer comprises stannide inclusions. Preferably the carbide inclusions are continuous extensions or projections of the bonding layer as they extend, substantially without interruption, from the intermediate carbide-rich, nickel-depleted bonding layer into the stannide phase, and the stannide inclusions are likewise continuous extending from the stannide layer into the intermediate carbide-rich, nickel-depleted bonding layer. The aforementioned presence of carbide inclusions in the stannide layer, and stannide inclusions in the intermediate carbide-rich, nickel-depleted bonding layer, provide improved anchoring of the protective layer thereby increasing abrasion resistance. The interface between the intermediate carbide-rich, bonding layer and the nickel-enriched stannide layer is irregular, but is otherwise substantially without interruption.

Although there is a need to ensure a complete coating of the underlying base metal to be protected, applying excessive amounts or thicknesses of the material used to form the protective layer must also be avoided. If the layer is too thick, for example, where the alloying materials of a prior have locally pooled prior to curing, liquid metal embrittlement can occur. The problem of liquid metal embrittlement is essentially one of eating through the metal with alloying materials (such as tin or germanium) which are extremely corrosive to steel under reducing conditions to the point where, again, the metallurgy fails.

Additionally, it has been found that certain preferred coatings are sulfur-tolerant, for example, the tin-based protective layers can tolerate up to 200 ppm sulfur. The protective layers eliminate the need to presulfide the metallurgy, reduce sulfide corrosion and improve product values and waste disposal due to induced levels of sulfur. Chromium-, Sb- and Ge-based protective layers can tolerate even higher sulfur levels, up to 5 or more wt. %. Most preferably, the layers can tolerate the respective amounts of sulfur for a period of at least 200, preferably at least 400, and most preferably 600 hours without degrading to an extent that carburization will occur, resulting in shut-down of the system due to excessive coking.

With the foregoing, as well as other objects, advantages, features and aspects of the disclosure that will become hereinafter apparent, the nature of the disclosure may be more clearly understood by reference to the detailed description and the appended claims.

DETAILED DESCRIPTION OF THE PREFERRED EMBODIMENTS

Figure 1:
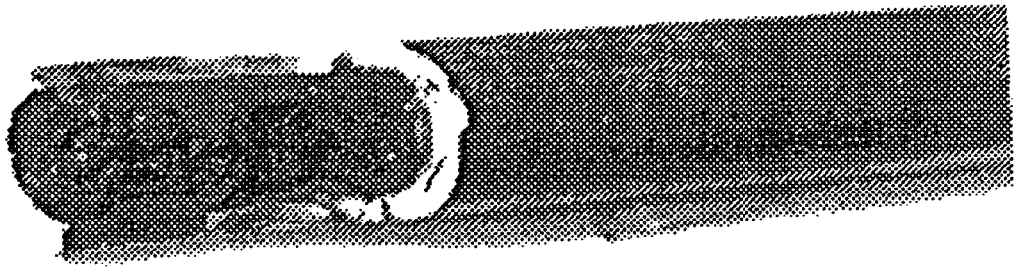
FIG. 1 is a photograph of a comparative thermal hydrodealkylation reactor which was completely plugged with coke during operation.

The following description of the method for inhibiting carburization, the process for thermally hydrodealkylating a hydrocarbon and the reactor system, are merely illustrative of the preferred embodiments of the present invention, and they should not be considered as limiting the scope of the invention in any way, as these illustrations and other equivalents thereof will become more apparent to those versed in the art in light of the present disclosure, and the accompanying claims.

As indicated above, the present disclosure provides a method for inhibiting carburization in a process for hydrodealkylating a dealkylatable hydrocarbon. The method includes pretreating surfaces of the reactor system with a metal which inhibits carburization under dealkylation conditions. Optionally, or in the alternative, the hydrodealkylation reactor system is treated with, or made of a composition which inhibits or reduces carburization and metal-dusting.

Essentially, the process of hydrodealkylating a dealkylatable hydrocarbon includes subjecting a gaseous mixture comprising the hydrocarbon and hydrogen in a reactor system at a temperature sufficient to convert the hydrocarbon to benzene and other by products.

In a preferred embodiment, benzene is produced from alkyl benzenes such as toluene according to the following overall reaction:

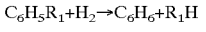

$$C_6H_5R_1+H_2 \rightarrow C_6H_6+R_1H$$

where $R_1$ is an alkyl group which is removed.

For mixed alkylbenzene feedstocks, $R_1$ may consist of one, two, three or four methyl groups; combinations of methyl and ethyl groups; or a single chain alkyl group containing one to four carbons. If the resultant gas is propane or butane, these compounds may be hydrocracked completely to methane and ethane under certain hydrodealkylation conditions. Substantial amounts of ethane am also converted to methane so that the process off-gas consists mainly of hydrogen and methane.

While not wishing to be bound by theory, the reaction mechanisms believed to occur during the production of benzene from alkyl benzenes are illustrated by the following:

I. Reaction A: Dealkylation of $C_9$ Benzene (Multiple Alkyl Groups)

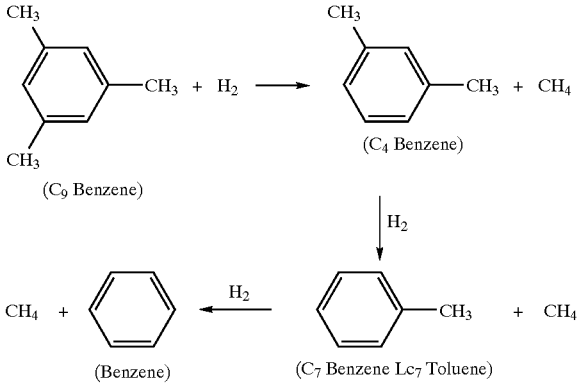

II. Reactance B: Dealkylation of $C_9$ Benzine (Single Alkyl Group)

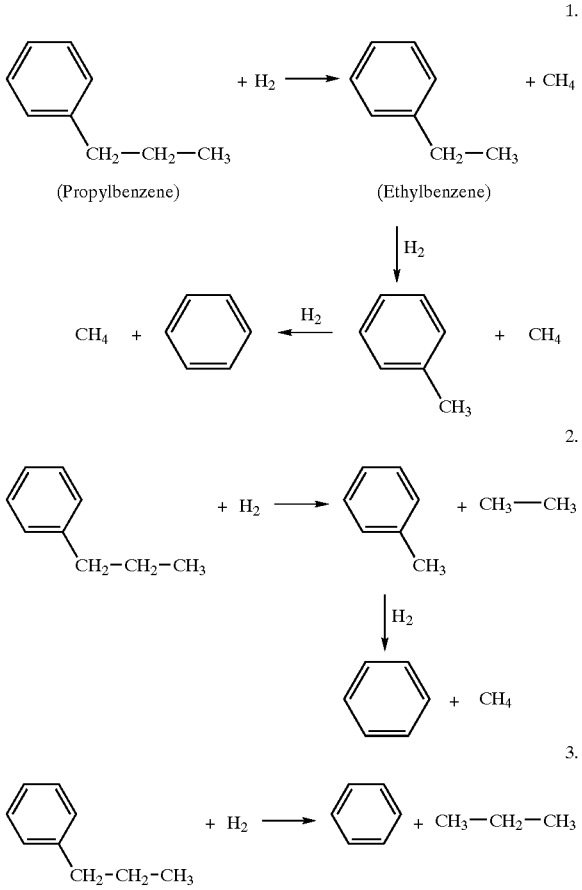

The ultimate products from all of these reactions are essentially benzene and an alkyl compound. Typically, under thermal hydrodealkylation conditions, the products from these reactions are essentially benzene and methane, since the propane and most of the ethane in subsequently cracked to methane to under reaction conditions.

Theoretically, one mole of benzene is formed from each mole of alkylbenzene that is completely dealkylated, and one mole hydrogen is consumed for each carbon in the alkyl group removed from the phenyl radical. However, the dealkylation reaction is not 100% selective, so products other than benzene may be formed. These other products typically result from condensation and cracking reactions.

Methane is typically a major byproduct from the hydrodealkylation process. Each methyl group removed during dealkylation results in the formation of methane. However, some methane is also produced by hydrocracking of the aromatic ring. Since the aromatic ring structure is very stable, even at the high temperatures used in thermal hydrodealkylation, only about 1% of the rings are destroyed by hydrocracking to methane. Additional methane is produced when the feedstock contains nonaromatics. At thermal hydrocracking condition, paraffins and naphthenes will be converted almost entirely to methane.

Hydrocracking reactions are big consumers of hydrogen and also release large quantities of heat which must be absorbed in a controllable manner. If substantial quantities of paraffins are to be charged, the thermal hydrodealkylation process must be designed to prevent an excessive temperature increase in the reactor by, for example, using a high recycle gas flow as a heat sink.

By "hydrodealkylatable hydrocarbon," as used herein, it is meant a hydrocarbon that when subjected to hydrodealkylation conditions in the presence of hydrogen, an alkyl group is removed. The alkyl-substituted benzenes, for example, toluene, m-xylene, o-xylene, p-xylene, mixed xylenes, ethyl benzene, propyl benzene, butyl benzene and other $C_7$–$C_{10}$ alkyl benzenes are of particular interest. The process is particularly suitable for the hydrodealkylation of toluene to benzene and methane.

By "hydrodealkylation conditions," as used herein, it is meant conditions sufficient to convert a hydrodealkylatable hydrocarbon such as an alkyl-substituted benzene to benzene and the resulting byproducts. Such conditions vary depending on the particular feed and process utilized; however, they are well known to those skilled in the art as represented by, for example, U.S. Pat. Nos, 2,929,775, 3,160,671, 3,284,526, 3,291,841, 3,607,960, 3,700,745, 3,835,183, 3,966,833, 4,058,452, 4,189,613, 4,19 1,632, 4,451,687 4,463,206 and 5,053,574, each of which are hereby incorporated by reference.

The process of the present invention is particularly suitable for use under "hydrodealkylating conditions" exhibiting temperatures of at least about 700° F., more preferably at least about 900° F., and even more preferably at least about 1100° F.

Most preferably, the process is a thermal process in the absence of a catalyst. Such a process may temperatures above about 900° F. Such a process can exhibit temperatures above about 1100° F. and below about 1800° F. At these temperatures, where carburization embrittlement and metal-dusting are significant problems, the protection of the present invention is particularly useful. Such processes are disclosed in U.S. Pat. Nos. 2,929,775, 3,160,671, 3,284,526, 3,291,849, 3,607,960 and 4,058,452, each of which are hereby incorporated-by reference.

By "low sulfur conditions," as used herein with respect to hydrodealkylation processes, it is meant feeds having a sulfur contest lower than about 100 ppm, more preferably, lower than about 50 ppm, more preferably lower than about 10 ppm, and even more preferably lower than about 5 ppm and even more preferably "sulfur free." Preferably, "low sulfur conditions" means sulfur is not added to prevent carburization, embrittlement and metal-dusting. However, feeds containing sulfur above 100 ppm may be utilized.

By "reactor system," as used herein in connection with hydrodealkylation, there is intended at least one hydrodealkylation reactor, its corresponding piping, furnaces, furnace tubes, heat exchangers, and the like. The aforementioned problems with low sulfur hydrodeaklation can be effectively addressed by a selection of an appropriate reactor system material for contact with the hydrocarbons during processing. Thus, by "surfaces susceptible to carburization," as used herein, there is intended at least those surfaces of the reactor system that are in contact with hydrocarbons during processing wherein carburization will take place under reaction conditions, and corresponding skin temperatures of the reactor system.

A solution to the problems of carburization and metal-dusting may involve the application to the surfaces exposed to the reaction of a coating which forms a protective layer resistant to carburization, metal-dusting and embrittlement. By "resistant to carburization, metal-dusting and embritlement," as used herein, it is meant those materials that will provide systems which have a resistance to embrittlement from carburization less than about 2.5 mm/year, preferably less than 1.5 mm/year, more preferably less than 1 mm/year, and most preferably less than 0.1 mm/year. Preventing embrittlement to such an extent will significantly reduce metal dusting and coking in the reactor system, and permits operation for longer periods of time.

Such coating may be thin aluminum or alumina films on, or the use of aluminized materials as, at least a portion of the metal surfaces in the reactor system. In fact, the metal surfaces particularly susceptible to carburization and metal-dusting can be provided in that manner. Such metal surfaces include but are not limited to, the reactor walls, furnace tubes, heat exchangers and the like.

When applying an aluminum or alumina film, it is preferable that the film have a thermal expensively that is similar to that of the metal surface to which it is applied (such as a mild steel) in order to withstand thermal shock or repeated temperature cycling. This prevents cracking or spilling of the film which could expose the underlying metal surface to the carburization inducing hydrocarbon environment.

Additionally, the film should have a thermal conductivity similar to that of, or exceeding, those of metals conventionally used in the construction of hydrodealkylation reactor systems. Furthermore, the protective layer derived from the aluminum or alumina film should not degrade in the hydrodealkylation environment or in the oxidizing environment associated with catalyst regeneration, nor should it result in the degradation of the hydrocarbons in the reactor system.

Suitable methods for applying aluminum or alumna films to metal surfaces such as mild steels include well known deposition techniques. Preferred processes include powder and vapor diffusion processes such as the "Alonizing" process, which has been commercialized by Alon Processing, Inc., Terrytown, Pa.

Essentially, "Alonizing" is a high temperature diffusion process which alloys aluminum into the surface of a treated metal, such as, e.g., a commercial grade mild steel. In this process, the metal (e.g., a mild steel) is positioned in a retort and surrounded with a mixture of blended aluminum powders. The retort is then hermetically sealed and placed in an atmosphere-controlled furnace. At elevated temperatures, the aluminum deeply diffuses into the treated metal resulting in an alloy. After furnace cooling, the substrate is taken out of the retort and excess powder is removed. Straightening, trimming, beveling and other secondary operations can then be performed as required. This process can render the treated ("alonized") metal resistant to carburization and metal-dusting under low sulfur hydrodealkylation conditions according to the invention.

Thin chromium or chromium oxide films can also be applied to metal surfaces of the reactor system to form protective layers resistant to carburization and metal-dusting under low sulfur hydrodealkylation conditions. Like the use of alumina and aluminum films, and aluminized materials, protective layers derived from chromium or chromium oxide coated metal surface have not been used to address carburization problems under low sulfur hydrodealkylation conditions.

Chromium or chromium oxide can also be applied to carburization and metal-dusting susceptible metal surfaces such as the reactor walls and furnace tubes, heat exchangers, and the like. However, any surface in the system which would show signs of carburization and metal-dusting under low sulfur hydrodealkylation conditions would benefit from the application of a thin chromium or chromium oxide film.

When applying the chromium or chromium oxide film, it is preferable that the chromium or chromium oxide derived protective layer have a thermal expansivity similar to that of the metal to which it is applied. Additionally, the chromium or chromium oxide derived protective layer should be able to withstand thermal shocks and repeated temperature cycling. This avoids cracking or spalling of the protective layer which could potentially expose the underlying metal surfaces to carburization inducing environments. Furthermore, the protective layer should have a thermal conductivity similar to or exceeding those materials conventionally used in hydrodealkylation reactor systems (in particular mild steels) in order to maintain efficient heat transfer. The protective layer also should not degrade in the hydrodealkylation environment or in the oxidizing environment associated with catalyst regeneration, nor should it induce degradation of the hydrocarbons in the reactor system.

Suitable methods for applying chromium or chromium oxide films to surfaces such as, e.g., mild steels, include well known deposition techniques. Preferred processes include powder-pack and vapor diffusion processes such as the "chromizing" process, which is commercialized by Alloy Surfaces, Inc., of Wilmington, Del.

The "chromizing" process is essentially a vapor diffusion process for application of chromium to a metal surface (similar to the above-described "Alonizing process"). The process involves contacting the metal to be coated with a powder of chromium, followed by a thermal diffusion step. This, in effect, creates an alloy of the chromium with the treated metal and renders the surface extremely resistant to carburization and metal-dusting under low sulfur hydrodealkylation conditions.

Resistant material systems which are preferred can be derived from copper, tin, arsenic, antimony, bismuth, chromium, germanium, gallium, indium, selenium, tellurium, lead and brass, and intermetallic compounds and alloys thereof (e.g., Cu—Sn alloys, Cu—Sb alloys, stannides, antimonides, bismuthides, etc). Steels and even nickel-rich alloys containing these metals can also show reduced carburization. In a preferred embodiment, the aforementioned materials are provided as a plating, cladding, paint (e.g., oxide paints) or other coating to a base construction material. This is particularly advantageous since conventional construction materials such as mild steels can still be used for processes below about 1150° F. with only the surface contacting the hydrocarbons being treated. Of these, tin is especially preferred as it reacts with the surface to provide a protective layer having excellent carburization resistance at higher temperatures, and which resists peeling and flaking. Also, it is believed that a tin derived protective layer can be as thin as 1/10 micron and still prevent carburization.

However, because the protective layers are exposed to the relatively harsh conditions of hydrodeakylation processes (e.g., high temperatures), the protective layers must be of sufficient thickness to provide a substantially complete coating of the underlying base metal. Even minor imperfections, pinholes or other flaws in the protective layer can provide destructive carburization sites sufficient to shut-down operation.

In fact, it has been observed that the interface between a stannide-protected portion of steel and an unprotected portion, relatively deep pitting and carburization attack occurs; surprisingly more so than anywhere else across the rest of the unprotected steel surface. This suggests that an incompletely protected system is even more vulnerable to metallurgical failure than a wholly protected system.

The application of excessive amounts or thicknesses of the material used to form the protective layer must also be avoided. If the layer is too thick liquid metal embrittlement can occur.

The protective layer must also maintain its integrity through operation. As such, the protective coating must be sufficiently abrasion resistant during catalyst loading, start-up, as well a during operation. This is achieved through appropriate anchoring of the protective layer to the steel substrate. According to the invention, the protective layer can be anchored to the steel substrate through an intermediate carbide-rich bonding phase.

As noted above, effective protective layers can be derived from a variety of metals such as tin, copper, arsenic, antimony, bismuth, chromium, brass, germanium, gallium, indium, selenium, tellurium, lead and intermetallic compounds and alloys thereof, more preferably tin, germanium, antimony, arsenic, selenium, chrome and tellurium. Of these, tin, germanium and antimony are more preferred, with tin being the most preferred. Gallium, lead, bismuth, brass, indium and copper are less preferred, with brass and copper being the least preferred. Lead, bismuth and Indium do not react with iron. They can be used on nickel-rich materials such as INCONEL 600 (75% Ni/16% chromium/9% Fe).

One of these is first applied to a portion (or portions) of a hydrodeakylation reactor system as a plating, cladding or coating to a thickness effective to provide a complete coating, while avoiding thicknesses at which liquid metal embrittlement will occur. Then the plating, cladding or coating is treated in a manner effective to form a protective layer which is anchored to the steel substrate thereby providing the necessary abrasion resistance. Preferably, the plating, cladding, or coating is resistant to abrasion, peeling or flaking for a period of 1 year, preferably 2 years, and more preferably 3 years such that the reactor system will maintain its carburization resistant properties without reapplication.

Multiple coatings can be applied. For example, a tin coating can be applied, and cured, followed by copper plating. Although, it has been found that copper is effective for preventing carburization and metal dusting, it does not generally adhere well to steel. Peeling and flaking of the copper is observed. However, if the steel surface is first coated with tin, then the copper plate will adhere well to the coating, and provide additional protection to the metal surface. In essence, the resulting stannide layer functions as a glue which adheres the copper plate to the underlying steel.

Forming a protective layer according to the invention will depend on temperature treatment after application of the aforementioned metals, and the nature of the base metal.

Taking the application of tin as an example, Ni3Sa, Ni3Sn2, and Ni3Sn4 can all be expected in nickel-rich systems, and Fe3Sn, Fe3Sn2, and FeSn in iron-rich systems. Under temperature exposures of from about 925° to 1200° F., one an expect an X3Sn2 solid solution on stainless steels. On nickel-free steels there is observed Fe3Sn2 overlain by FeSn. Below 925° F. one can expect FeSn2 but not Fe3Sn2. On stainless steels them is observed FeSn overlain by FeSn2 overlain by Ni3Sn4. At high temperatures, e.g., 1600° F., there can be found (Ni,Fe)3Sn and (Ni,Fe)3Sn2 on stainless steels, but no steel-tin alloy, while on nickel-free steels there is found a diffusion layer of iron-tin alloy overlain by the phases Fe3Sn and Fe3Sn2.

A preferred embodiment of the invention uses a reactor system including a stainless steel portion, which comprises providing the stainless steel portion with a stannide protective layer of sufficient thickness to isolate the stainless steel portion from hydrocarbons, which protective layer is anchored to the steel substrate through an intermediate carbide-rich, nickel-depleted stainless steel bonding layer. More particularly, the stannide layer is nickel-enriched and comprises carbide inclusions, while the intermediate carbide-rich, nickel-depleted bonding layer comprises stannide inclusions. More preferably the carbide inclusions are continuous as they extend, substantially without interruption, from the intermediate carbide-rich, nickel-depleted bonding layer into the stannide phase, and the stannide inclusions are likewise continuous extending from the stannide layer into the intermediate carbide-rich, nickel-depleted bonding layer. The interface between the intermediate carbide-rich, nickel-depleted bonding layer and the nickel-enriched stannide layer is irregular, but is otherwise substantially without interruption. The extent to which the aforementioned phases, layers and inclusions develop are a function of the reducing conditions and temperature at which the initial plating, cladding a other coating is treated, and the amount of time at which exposure is maintained.

If steel stress relief techniques are used when assembling a reactor system, the production of iron oxides prior to application of the resistant plating, cladding or coating should be minimized. This can be accomplished by using a nitrogen atmosphere during steel stress relief (e.g., at 1650° F.).

In some instances applying a coating of the aforementioned elements as metals or reducible oxides, will not be particularly preferred. That is, to provide a good coating it is necessary that the material be molten. Unfortunately, some metals such as germanium, and to some extent antimony, have melting points which exceed levels which are practical, or even attainable, with a particular piece of equipment or apparatus. In those instances it is desirable to use compounds of those elements which have lower melting points.

For example, sulfides of antimony and germanium have lower melting points than their respective metals and can be used to produce antimonide and germanide coatings on steels in a $H_2$-rich, or perhaps even a non-reducing, atmosphere. Such sulfides can be used in the form of powders or paints which react to produce antimonide and germanide coatings at significantly lower temperatures than those required for the metals. Tests have shown that antimonide coatings can be applied to 300 series stainless steel and INCOLOY 800 using $Sb_2S_3$ powder at 1030° F. in 20 hours of curing under an atmosphere of 7% $C_3H_8$ to $H_2$. Also, tests have shown that germanide coatings can be applied to INCOLOY 800 using $GeS_2$ powder at 1150° F. under the same condition.

Where practical, it is preferred that the resistant materials be applied in a paint-like formulation (hereinafter "paint") to a new or existing reactor system. Such a paint can be sprayed, brushed, pigged, etc. on reactor system surfaces such as mild steels of stainless steels, and will have viscosity characteristics sufficient to provide a substantially continuous coating of measurable and substantially controllable thickness.

Chromium paints are also especially useful in this invention. The use of paints containing chromium halides is preferred, especially chromium chlorides ($CrCl_2$ and $CrCl_3$). Paints based on chromium halides appear to be self-fluxing and form strongly adherent coatings. One advantage of the chromium coatings is that they do not result in liquid metal embrittlement. Chromium paints are preferably reduced at higher temperatures than tin paints in order to produce metallic chromium-containing coatings. Useful reduction temperatures are above 1200° F., preferably at about 1400° F. or higher.

An example of a useful paint would be one comprising a fusible $CrCl_2$ salt which may or may not be incorporated with solvents and other additives. Other specific formulations include finely ground $CrCl_3$ in 90 wt. gear oil to form a viscous liquid, and finely ground $CrC_2$ in a petroleum jelly carrier. Such a paint provides a simple low cost method of applying chromium to steel, as it provides clean contact with the steel substrate which permits curing procedures to firmly attach the chromium to the steel. As an example, the paint can be reduced in $H_2$ or another suitable gas at about 1500° F. for 1 hours.

It is most preferred that such a paint be a decomposable, reactive, tin-containing paint which reduces to a reactive tin and forms metallic stannides (e.g., iron stannides and nickel/iron stannide) upon heating in a reducing atmosphere (e.g., an atmosphere containing hydrogen and possibly hydrocarbons such as carbon monoxide, etc.).

It is preferred that the aforementioned paint contain at least four components (or their functional equivalents); (i) a hydrogen decomposable tin compound, (ii) a solvent system, (iii) a finely divided tin metal and (iv) tin oxide as a reducible sponge/dispersing/binding agent. The paint should contain finely divided solids to minimize settling, and should not contain non-reactive materials which will prevent reaction of reactive tin with surfaces of the reactor system.

As the hydrogen decomposable tin compound, tin octanoate or neodecanoate is particularly useful. Commercial formulation of this compound itself are available and will partially dry to an almost chewing-gum-like layer on a steel surface; a layer which will not crack and/or split. This property is preferable for any coating composition used in this context because it is conceivable that the coated material will be stored for months prior to treatment with hydrogen. Also, if parts are coated prior to assembly they must be resistant to chipping during construction. As noted above, tin octanoate is available commercially. It is reasonably priced, and will decompose smoothly to a reactive tin layer which forms iron stannide in hydrogen at temperatures as low as 600° F.

Tin octanoate should not be used alone in a paint since it is not sufficiently viscous. Even when the solvent is evaporated therefrom, the remaining liquid will drip and run on the coated surface. In practice, for example, if such were used to coat a horizontal tube, it would pool at the bottom of the tube.

Component (iv), the tin oxide sponge/dispersing/binding agent, is a porous tin-containing compound which can sponge-up an organo-metallic tin compound, yet still be reduced to active tin in the reducing atmosphere. In addition, tin oxide can be processed through a colloid mill to produce very fine particles which resist rapid settling. The addition of tin oxide will provide a paint which becomes dry to the touch, and resists running.

Unlike typical paint thickeners, component (iv) is selected such that it becomes a reactive part of the coating when reduced. It is not inert like formed silica; a typical paint thickener which would leave an unreactive surface coating after treatment.

Finely divided tin metal, component (iii), is added to insure that metallic tin is available to react with the surface to be coated at as low a temperature as possible, even in a non-reducing atmosphere. The particle size of the tin is preferably one to five microns which allows excellent coverage of the surface to be coated with tin metal. Non-reducing conditions can occur during drying of the paint and welding of pipe joints. The presence of metallic tin ensures that even when part of the coating is not completely reduced, tin metal will be present to react and form the desired stannide layer.

The solvent should be non-toxic, and effective for rendering the paint sprayable and spreadable when desired. It should also evaporate quickly and have compatible solvent properties for the hydrogen decomposable tin compound. Isopropyl alcohol is most preferred, while hexane and pentane can be useful, if necessary. Acetone, however, tends to precipitate organic tin compounds.

In one embodiment, there can be used a tin paint of 20 percent Tin Ten-Cem (contains 20% tin as stannous octanoate in octanoic acid or neodecanoate in neodecanoic acid), stannic oxide, tin metal powder and isopropyl alcohol.

Iron bearing reactive paints are also useful in the processes of the invention. Such an iron bearing reactive paint will preferably contain various tin compounds to which iron has been added in amounts up to one third Fe/Sn by weight.

The addition of iron can, for example, be in the form of $Fe_2O_3$. The addition of iron to a tin containing paint should afford noteworthy advantages; in particular: (i) it should facilitate the reaction of the paint to form iron stannides thereby acting as a flux; (ii) it should dilute the nickel concentration in the stannide layer thereby providing better protection against coking; and (iii) it should result in a paint which affords the anti-coking protection of iron stannides even if the underlying surface does not react well.

In addition to applied thickness, viscosity and other properties of the paint are important. The viscosity should be such that the paint can be easily applied and that it does not drip or pool due to gravity. The paint should also be dryable once applied to the reactor surfaces. The thickness of the paint after application should be between 0.5 and 1.5 mils, preferably between 1 and 10 mils, and more preferably between 2 and 8 mils.

The metallic coatings and, in particular, the paints, are preferably produced under reducing conditions with hydrogen. Curing is preferably done in the absence of hydrocarbons. When tin paints are applied at the above-described thicknesses, initial reduction conditions will result in tin migrating to cover small regions (e.g., welds) which were not painted. This will completely coat the base metal. This curing results, for example, in a strong protective layer preferably between 0.5 and 10 mils thick, and more preferably between 1 and 4 mils thick comprising intermetallic compounds. In the case of tin, stannide layers such as iron and nickel stannides are formed. Microscopic analysis can readily determine the thickness of this layer. For ease of measurement of paint and coating thickness, coupons can be prepared which correspond to the painted reactor surface. These can be treated under identical conditions to the reactor system treatment. The coupons can be used to determine paint and coating thickness.

For tin-containing paints, it is preferable to initially cure the paint at temperatures below typical operating temperatures for hydrodealkylation. Curing temperature between 500° and 1100° F., preferably between 900° and 1000° F. (especially for oxide-containing paints), provide a carburization-resistant coating that minimizes the incorporation of chromium in the stannide coating (which is undesirable).

As an example of a suitable paint cure, the system including painted portions can be pressurized with $N_2$, followed by the addition of $H_2$ to a concentration greater than or equal to 50% $H_2$. The reactor inlet temperature can be raised to 800° F. at a rate of 50°–100° F. Thereafter the temperature can be raised to a level of 950°–975° F. at a rate of 50° F./hr, and held within that range for about 48 hours. Curing can also be achieved in pure $H_2$ at 1000° F. to 1200° F. for 2–24 hours.

As noted previously, for stannide protective layers curing temperature will affect the characteristics of the phases of the protective layer. Hence, care should be taken in curing the protective layer. For example, in the case of a stannide protective layer applied by plating tin on an INCOLOY 800 substrate (a nickel-rich steel), exposure to low curing temperatures, i.e., three weeks at 650° F. was observed to produce discrete iron and nickel stannide phases; with an unacceptably reactive nickel phase on the exterior. However, exposure at higher temperatures, i.e., one week at 650° F. followed by two weeks at 1000° F., was observed to provide acceptable stannide phases where the stannide was reconstituted to comparable nickel and iron abundance in each stannide phase. Exposure to even higher temperatures, i.e., one week at 650° F. followed by one week at 1000° F. and one week at 1200° F., showed a reconstitution of the stannide layer and carbide-rich under layer, to produce potentially reactive nickel-rich stannides, particularly on the surface of the protective layer. In this regard, it is believed that inclusion of iron, for example, in a paint formulation can be an effective counter-measure when curing at high temperatures.

The metal or metal compounds contained in the plating, cladding or other coating are preferably cured under conditions effective to produce molten metals and/or compounds. Thus, germanium and antimony paints are preferably cured between 1000° F. and 1400° F.

A test was conducted where unpainted steel samples were placed in reactors that had been treated with a tin-based paint like those described above, prior to reduction of the paint. The unpainted samples were nevertheless found to have uniform coatings of protective stannide after reduction. Thus, the aforementioned tin-containing paints, or other carburization resistant platings, claddings or coatings, can also be touched-up according to the invention. For example, a touch-up protective tin-based, antimony-based, germanium-based, etc., coating can be formed by injecting a fine powder of the metal, metal oxide, or other reactive compound of the metal, in a reducing gas stream containing $H_2$ and possibly hydrocarbons. Because of the migration characteristics of these metals, they will allow a fine mist of reactive liquid metal to react with exposed steel surfaces. In using the touch-up technique, catalyst beds should be removed a otherwise protected. It follows that the above-described technique could be used to provide original protective coatings, as well.

Tin derived coking and carburization protection of steel can also be applied, re-applying and/or touched-up by using tin halides at elevated temperatures, preferably touch-up of coated steel. Tin metal reacts with, for example, HCl to form volatile tin chlorides which disperse over steel and react to form protective iron/nickel stannides. Tin volatiles can be controlled by varying temperature and halide composition.

The technology associated with the invention can also be used for retrofitting previously carburized systems. For example, one of the aforementioned protective layers can be formed on a previously carburized surface by a suitable deposition technique such as chemical vapor deposition, or, if physically possible, by applying a paint of one or more of the materials described herein.

In retrofitting a previously carburized system, the protective layer should have a thermal expansivity close to that of the base metal, and should be able to withstand thermal shock and repeated temperature cycling, so the layer will not crack or spill and expose the base metal to the environment. In addition, the layer should have a thermal conductivity near or above those of commonly employed metals to maintain efficient heat transfer. The layer should not degrade in the environment nor in the oxidizing environment associated with common catalyst regeneration (coke bum-off), nor cause degradation of the hydrocarbons themselves.

Before retrofitting by creating the protective layer, coke should be removed from the surface of the base metal as it may interfere with the reaction between the protective layer and the base metal. A number of cleaning techniques are possible including (i) oxidizing the metal surface, (ii) oxidizing the metal surface and chemically cleaning, (iii) oxidizing the metal surface, and chemically cleaning followed by passivation, and (iv) oxidizing the metal surface and physically cleaning. Technique (i) is useful to remove residual coke and would be acceptable if the oxide layer was thin enough to allow a protective layer such as a stannide layer to form properly. The other techniques, therefore, are more preferred as they should remove the, oxide layer to prevent interference with the formation of an effective protective layer. Of course, combinations of the aforementioned cleaning techniques in a particular plant, or for a particular system, can be used. Ultimately a number of factors unique to the particular plant or system, such as reactor geometry, will dictate the choice.

Another potentially useful method for applying protective layers of carburization resistant materials is chemical vapor deposition ("CVD"). CVD techniques can be used in new or existing plants. CVD would be particularly useful in existing plants where other techniques prove to be difficult or impossible.

A preferred CVD technique involves vaporizing an organometallic compound containing one or more of the protective materials described herein in a hydrogen or hydrogen/inert gas mixture. Examples of such organometallic compounds include copper naphthenate, tetramethyl tin, tetrabutyl tin, triphenyl arsine, tributylantimony, bismuth neodecanoate, and chromium octanoate. The saturate gas should be heated so the organometallic compound will decompose on the base material. This approach would work particularly well in a temperature controlled furnace. The optimum conditions for the decomposition reaction will depend on the particular organometallic compound used.

Yet another means for preventing carburization, coking, and metal-dusting in the reactor system comprises the application of a metal costing or cladding to chromium rich steels contained in the reactor system. These metal coatings or claddings may be comprised of tin, antimony, germanium, bismuth or arsenic. Tin is especially preferred. These coatings or claddings may be applied by methods including electroplating, vapor depositing, and soaking of the chromium rich steel in a molten metal bath.

It is believed that in hydrodealkylation reactor systems where carburization, coking, and metal-dusting are particularly problematic, the coating of the chromium-rich, nickel-containing steels with a layer of tin in effect creates a double protective layer. There results an inner chromium rich and nickel poor layer which is resistant to carburization, coking, and metal-dusting and an outer stannide layer which is also resistant to carburization, coking and metal-dusting. This occurs because when the tin coated chromium rich steel is exposed to typical hydrodealkylation skin temperatures, such as up to about 1400° F., it reacts with the steel to form nickel-enriched iron nickel stannides. Thereby, the nickel is preferentially leached from the surface of the steel leaving behind a layer of chromium-rich layer. In some instances, it may be desirable to remove the iron nickel stannide layer from the stainless steel to expose the chromium-rich layer, or add iron to produce iron stannides.

For example, it was found that when a tin cladding was applied to a 304 grade stainless steel and heated at about 1200° F. there resulted a chromium-rich, carbide-rich layer under a stannide layer containing about 17% chromium and substantially no nickel, comparable to 430 grade stainless steel.

When applying the tin metal coating or cladding to the chromium-rich steel, it may be desirable to vary the thickness of the metal coating or cladding to achieve the desired resistance against carburization, coking, and metal-dusting. This can be done by, e.g., adjusting the amount of time the chromium-rich layer is soaked in a molten tin bath. This will also affect the thickness of the resulting chromium rich steel layer. It may also be desirable to vary the operating temperature, or to vary the composition of the chromium rich steel which is coated in order to control the chromium concentration in the chromium-rich layer produced.

It has additionally been found that tin-coated steels can be further protected from carburization, metal-dusting, and coking by a post-treatment process which involves application of a thin oxide coating, preferably a chromium oxide, such as $Cr_2O_3$. This coating will be thin, as thin as a few $\mu$m. Application of such a chromium oxide will protect aluminum as well as tin coated steels, such as Alonized steels, under low sulfur conditions.

The chromium oxide layer can be applied by various methods including: application of a chromate or dichromate paint followed by a reduction process; vapor treatment with an organo-chromium compound; or application of a chromium metal plating followed by oxidation of the resulting chromium plated steel.

"Alonized" steels which are resistant to carburization under hydrodealkylation conditions can be rendered further resistant by post-treatment of the aluminum coated steel with a coating of tin. This results in a steel which is more carburization resistant since there are cumulative effects of carburization resistance obtained from both the aluminum coating and the tin coating. This post-treatment affords an additional benefit in that it will mend any defects or cracks in the aluminum, e.g., Alonized, coating. Also, such a post-treatment should result in a lower cost since a thinner aluminum coating can be applied to the steel surface which is to be post-treated with the tin coating. Additionally, this post-treatment will protect the underlying steel layer exposed by bending of aluminized steels, which can introduce cracks in the aluminum layer, and expose the steel to carburization induced under high temperature conditions. Also, this post-treatment process can prevent coke formation on the treated steel surfaces and also prevent coke formation that occur on the bottom of cracks which appear on steels which have been aluminized, but not additionally coated with tin.

While not wishing to be bound by theory, it is believed that the suitability of various materials can be selected and classified according to their responses to carburizing atmospheres. For example, iron, cobalt, and nickel form relatively unstable carbides which will subsequently carburize, coke and dust. Elements such as chromium, niobium, vanadium, tungsten, molybdenum, tantalum and zirconium, will form stable carbides which are more resistant to carburization, coking and dusting. Elements such as tin, antimony, germanium and bismuth do not form carbides or coke. And, these compounds can form stable compounds with many metals such as iron, nickel and copper under hydrodealkylation conditions. Stannides, antimonides and bismuthides, and compounds of lead, mercury, arsenic, germanium, indium, tellurium, selenium, thallium, sulfur and oxygen are also resistant. A final category of materials include elements such a silver, copper, gold, platinum and refractory oxides such a silica and alumina. These materials are resistant and do not form carbides, or react with other metals in a carburizing environment under hydrodealkylation conditions.

As discussed above, the selection of appropriate metals which form protective layers resistant to carburization and metal-dusting, and their use to form protective layers on metal surfaces in the reactor system, is one means for preventing the problems of carburization and metal-dusting. However, carburization and metal-dusting can be prevalent in a wide variety of metals; and the metals can be more costly or exotic than conventional materials (e.g., mild steels) used in the construction of reactor systems. Accordingly, it may be desirable in the reactor system of the invention to use ceramic materials which do not form carbides at typical conditions, and thus are not susceptible to carburization, for at least a portion of the metal surfaces in the reactor system.

In choosing the ceramic materials for use in the process of the present disclosure, it is preferable that the ceramic material have thermal conductivities about that or exceeding those of materials conventionally used in the construction of hydrodealkylation reactor systems. Additionally, the ceramic materials should have sufficient structural strengths at the temperatures which occur within the hydrodealkylation reactor system. Further, the ceramic materials should be able to withstand thermal shocks and repeated temperature cycling which occur during operation of the reactor system. Additionally, the ceramic surface should not be susceptible to degradation in the hydrocarbon environment or in the oxidizing environment. The selected ceramic material also should not promote the degradation of the hydrocarbons in the reactor system.

Suitable ceramic materials include, but are not restricted to, materials such as silicon carbides, silicon oxides, silicon nitrides and aluminum nitrides. Of these, silicon carbides and silicon nitrides are particularly preferred as they appear capable of providing complete protection for the reactor system, even under low sulfur hydrodealkylation conditions.

At least a portion of the metal surfaces in the reactor system can also be coated with a silicon or silica film. In particular, the metal surfaces which can be coated include, but are not limited to the reactor walls. However, any metal surface in the reactor system, which shows signs of carburization and metal-dusting would benefit from the application of a thin silicon or silica film.

Conventional methods can be used for applying silicon or silica films. Silica or silicon can be applied by electroplating and chemical vapor deposition of an alkoxysilane in a steam carrier gas. It is preferable that the silicon or silica film have a thermal expansivity about that of the metal surface which it coats. Additionally, the silicon or silica film should be able to withstand thermal shocks and repeated temperature cycling that occur during hydrodealkylation. This avoids cracking a spelling of the silicon or silica film, and potential exposure of the underlying metal surface to the carburization inducing hydrocarbon environment. Also, the silica or silicon film should have a thermal conductivity approximate to or exceeding that of metals conventionally used in hydrodealkylation reactor systems so as to maintain efficient heat transfer. The silicon or silica film also should not degrade in the hydrodealkylation environment or in an oxidizing environment; nor should it cause degradation of the hydrocarbons themselves.

Because different areas of the reactor system of the invention can be exposed to a wide range of temperatures, the material selection can be staged, such that those materials providing protective layers with better carburization resistances are used in those areas of the system experiencing the highest temperatures.

With regard to materials selection, it was discovered that oxidized Group VIII metal surfaces such as iron, nickel and cobalt are more active in terms of coking and carburization than their unoxidized counterparts. For example, it was found that an air roasted sample of 347 stainless steel was significantly more active than an unoxidized sample of the same steel. This is believed to be due to a re-reduction of oxidized steels which produces very fine-grained iron and/or nickel metals. Such metals are especially active for carburization and coking.

Since the techniques described herein can be used to control carburization, catalytic coking, and metal dusting at high temperatures, they can be used in other areas of chemical and petrochemical processing, as well. These areas would include high temperature chemical and petrochemical processing where the carburization phenomena has previously been recognized, as well as lower temperature processes, which until recently, have not exhibited excessive carburization related problems.

For example, the teachings can be applied to any furnace tubes which are subjected to carburization, catalytic coking and metal dusting, such as furnace tubes in coker furnaces. Additionally, the techniques can be used to control carburization, catalytic coking, and metal dusting in cracking furnaces operating at from about 1400° to about 1700° F. For example, the deterioration of steel occurring in cracking furnaces operating at those temperatures can be controlled by application of various metal-based protective layers. These protective layers can be provided by applying metals using melting, electroplating, and painting techniques. Painting is particularly preferred.

A coating of antimony applied to iron bearing steels protects these steels from carburization, coking and metal dusting under the described cracking conditions. In fact, an antimony paint applied to iron bearing steels will provide protection against carburization, catalytic coking, and metal dusting at 1600° F.

A coating of bismuth applied to nickel rich steel alloys (e.g., INCONEL 600) can protect those steels against carburization, catalytic coking, and metal dusting under cracking conditions. This has been demonstrated at temperatures of up to 1600° F.

Bismuth coatings may also be applied to iron bearing steels and provide protection against carburization, metal dusting, and catalytic coking under cracking conditions. Also, a metal coating comprising a combination of bismuth, antimony, and/or tin can be used.

The aforementioned chromium paint could also be applied to steel tubes and reduced in-situ for use in ethane cracking furnaces. In essence, the chromium paint can provide a refractory surface in numerous environments such as carburizing, oxidizing and chloriding environments.

Chromium-plated steels are also likely to be useful in other environments as they have been found to also exhibit carburization and catalytic coking resistance in high temperature environments (e.g., 800° F.–2000° F.). That is, in a cracking environment of 2000° F. for 1 hour in a carburizing gas of 7% $C_3H_8$ in $H_2$ bubbled through HO doped with sufficient $CS_2$ to provide approximately 100 ppm sulfur, a chromium plated 304 stainless steel sample did not exhibit coking or carburization, whereas an untreated sample of INCOLOY 800, and samples of stannided and antimonided nickel-plated INCOLOY 800 did exhibit coking. In the complete absence of sulfur, the chromium-plated sample did exhibit coking, but much less than the untreated sample.

In the aforementioned test, chromium was applied as a plating and beat treated to weld or glue the chromium to the steel. The chromium plate was found to have reacted with the steel substrate to form a glue composed of CrFe and chromium carbide; with a coating of $Cr_2O_3$ forming on the exterior. For further resistance, the surface of the chromium plated steel can be antimonided or germanided.

The technology is also useful is conventional and low-sulfur reforming processes which involve substantially lower temperatures. It has recently been found that conventional reforming processes were operated in the presence of enough sulfur that carburization, metal dusting and catalytic coking were not observed problems. With the advent of low-sulfur systems, problems emerged.

In ultra "low-sulfur" reforming systems, the feeds typically contain less than 100 ppb sulfur, more preferably, less than 50 ppb sulfur, and even more preferably, less than 25 ppb sulfur such as lane than 5 ppb sulfur ("ultra, ultra-low sulfur"); an insufficient amount to interfere with carburization. Substantially more sulfur is present in conventional (i.e., non-low-sulfur) catalytic reforming techniques. In this regard, the world-wide average is around 500 ppb sulfur, and even higher levels are common. It is possible that a conventional feed can reach 1,000–5,000 ppb sulfur during upset conditions.

Even though both conventional and low-sulfur reforming systems involve relatively low temperatures compared to e.g., ethane cracking processes, excessively high temperatures can still occur in the catalyst beds when exothermic demethanation reactions within cokeballs cause localized hot regions. These hot spots pose a source for a carburization related problem in even conventional reforming reactor systems where substantial amounts of sulfur are present.

For example, the center pipe screens of reformers have been observed to locally waste away and develop holes; ultimately resulting in catalyst migration. In conventional reforming processes the temperatures within cokeballs during formation and burning are apparently high enough to overcome the ability of process sulfur to poison catalytic coking, carburization, and dusting. The metal screens, therefore, carburize and are more sensitive to wasting by intergranular oxidation (a type of corrosion) during regeneration. The screen openings enlarge and holes develop.

If used to treat screens in conventional reforming, a chrome-based passivation layer would likely be more desirable than one which is tin-based, as such a layer should withstand catalyst regeneration in air and redispersion with chlorides. Chromium would likely be more robust than tin under such conditions. In this regard, tests suggest that a chrome plating is more resistant to metal migration (loss) during rejuvenation, and a chrome plating would be harder making it less likely to rub off during catalyst loading.

Accordingly, the technology associated with the present invention would be useful in any hydrocarbon conversion process where it becomes desirable to reduce the amount of sulfur and/or water, present e.g., in the feed or injected separately, to levels less than those conventionally used. In this regard, if the technology of the invention is applied to other chemical and petrochemical processes, "low-sulfur" will be a level of sulfur less than that found in a conventional feed or reactor system during processing for a particular process (e.g., steps have been taken to lower the levels of sulfur in the feed or reactor system, or no or little sulfur is added during the process. The technology of the present invention could provide means for lowering operating costs of such processes, which costs were previously inflated due to the presence of sulfur and/or water, as well as a means to provide significant improvements in catalyst performance as sulfur tends to poison or deactivate most all catalysts to some degree. Likewise, the technology associated with the invention would be useful in processes where carburization, coking and/or metal dusting problems exist now, and new techniques are needed to effectively address those problems.

Examples of processes where the technology associated with the invention could potentially be useful include, but are not limited to, nonoxidative and oxidative dehydrogenation of hydrocarbons to olefins and dienes, dehydrogenation of ethylbenzene to styrene, conversion of light hydrocarbons (i.e., $C_2$–$C_5$, preferably $C_3$–$C_4$) to aromatics, transalkylation of toluene to benzene and xylenes, dealkylation of alkylaromatics to aromatics, alkylation of aromatics to alkylaromatics, production of fuels and chemicals from $H_2$ and CO (e.g., the Fischer-Tropsch process), steam reforming of hydrocarbons to $H_2$ and CO, the production of diphenylamine from aniline, methanol alkylation of toluene to xylenes, and dehydrogenation of isopropyl alcohol to acetone. Technical details regarding the aforementioned processes can be found in Kirk-Othmer—Encyclopedia of Chemical Technology, Third Edition, 1978, the contents of which is hereby incorporated by reference.

Preferred processes in which the technology of the invention can be useful include the conversion of light hydrocarbons to aromatics, production of fuels and chemicals from $H_2$ and CO, and steam reforming of hydrocarbons to $H_2$ and CO.

Looking again to hydrodeakylation processes, other techniques can also be used to address the problems associated with carburization, embrittlement and metal-dusting. They can be used in conjunction with an appropriate material selection for the reactor system. Preferred from among the additional techniques is the addition of non-sulfur, anti-carburizing and anti-coking agent(s) during the hydrodealkylation process. These agents can be added continuously during processing and function to interact with those surfaces of the reactor system which contact the hydrocarbons, or they may be applied as a pretreatment to the reactor system, to the extent they can be applied as a complete coating, or as a supplement to other treatment.

While not wishing to be bound by theory, it is believed that these agents interact with the surfaces of the reactor system by decomposition and surface attack to form iron and/or nickel intermetallic compounds, such as stannides, antimonides, germanides, bismuthides, plumbides, antimonides, etc. Such intermetallic compounds an resistant to carburization, coking and dusting and can protect the underlying metallurgy.

The intermetallic compounds are also believed to be more stable than the metal sulfides which were formed in systems where $H_2S$ was used to passivated the metal. These compounds are not reduced by hydrogen as are metal sulfides. As a result, they are less likely to leave the system than metal sulfides. Therefore, the continuous addition of a carburization inhibitor with the feed can be minimized.

Preferred non-sulfur anti-carburizing and anti-coking agents include organo-metallic compounds such as organo-tin compounds, organo-antimony compounds, organo-germanium compounds, organo-bismuth compounds, organo-arsenic compounds, and organo-lead compounds. Suitable organo-lead compounds include tetraethyl and tetramethyl lead. Organo-tin compounds such as tetraethyl tin and trimethyl tin hydride are especially preferred.

Additional specific organo-metallic compounds include bismuth neodecanoate, chromium octanoate, copper naphthenate, manganese carboxylate, palladium neodecanoate, silver neodecanoate, tetrabutylgermanium, tributylantimony, triphenylantimony, triphenylarsine, and zirconium octanoate.

How and where these agents are added to the reactor system is not critical, and will primarily depend on particular process design characteristics. For example, they can be added continuously or discontinuously with the feed.

A preferred method of coating the agents on an existing or new reactor surface is to decompose an organometallic compound in a hydrogen atmosphere at temperatures of about 900° F. For organo-tin compounds, for example, this produces reactive metallic tin on the reactor surface. At these temperatures, the tin will further react with the surface metal to passivate it.

Optimum coating temperatures will depend on the particular organometallic compound, or the mixtures of compounds if alloys are desired. Typically, in excess of the organometallic coating agent can be pulsed into the reactor at a high hydrogen flow rate so as to carry the coating agent throughout the system in a mist. The flow rate can then be reduced to permit the coating metal mist to coat and react with the reactor surface. Alternatively, the compound can be introduced as a vapor which decomposes and reacts with the hot walls of the reactor in a reducing atmosphere.

As discussed above, hydrodealkylation reactor systems susceptible to carburization, metal-dusting and coking can be treated by application of a decomposable coating containing a decomposable organometallic tin compound to those areas of the reactor system most susceptible to carburization.

However, such control is not always present. There may be "hot spots" which develop in the reactor system where the organometallic compound can decompose and form deposits. Therefore, another aspect of the invention is a process which avoids such deposition in hydrodealkylation reactor systems where temperatures are not closely controlled and exhibit areas of high temperature hot spots.

Such a process involves preheating the entire reactor system to a temperature of from 750° to 1150°, preferably 900° to 1100°, and most preferably about 1050° F., with a hot stream of hydrogen gas. After preheating, a colder gas stream at a temperature of 400° to 800°, preferably 500° to 700°, and most preferably about 550° F., containing a vaporized organometallic tin compound and hydrogen gas is introduced into the preheated reactor system. This gas mixture is introduced upstream and can provide a decomposition "wave" which travels throughout the entire reactor system.

Essentially this process works because the hot hydrogen gas produces a uniformly heated surface which will decompose the colder organometallic gas as it travels as a wave throughout the reactor system. The colder gas containing the organometallic tin compound will decompose on the hot surface and coat the surface. The organometallic tin vapor will continue to move as a wave to treat the hotter surfaces downstream in the reactor system. Thereby, the entire reactor system can have a uniform coating of the organometallic tin compound. It may also be desirable to conduct several of these hot-cold temperature cycles to ensure that the entire reactor system has been uniformly coated with the organometallic tin compound.

To obtain a more complete understanding of the present disclosure, the following examples illustrating certain aspects of the invention are set forth. It should be understood, however, that the disclosure is not limited in any way to the specific details set forth therein.

Comparative Example 1

A thermal hydrodealkylation reactor made of 0.25 inch OD 316 stainless steel seamless pipe 8.75 inches long was prepared by cleaning the surfaces of the reactor exposed to the hydrodealkylation reaction with soap and water, and drying with an organic solvent. The reactor was preheated and maintained al 1250° F. Toluene at 25 μl/min was fed into the reactor with hydrogen at 20 cc/min. The reactor pressure was maintained at approximately 100 psig. The reactor was completely plugged with coke formed by carburization when checked after 65.6 hours of operation.

Comparative Example 2

A thermal hydrodealkylation reactor was prepared as described in Comparative Example 1. The reactor was pretreated and maintained at 1400° F. Again, toluene at 25 μl/min was fed into the reactor with hydrogen at 20 cc/min. The reactor pressure was maintained at approximately 100 psig. The reactor was completely plugged with coke due to carburization when checked after 5.7 hours of operation. See FIG. 1, which is a photograph of the reactor partially cut open to show the coke plug.

EXAMPLE 1

A thermal hydrodealkylation reactor made of 0.25 inch OD 316 stainless steel seamless pipe 8.75 inches long was prepared by cleaning the surfaces of the reactor exposed to the hydrodealkylation reaction with soap and water, and drying with an organic solvent. The reactor was then coated by pouring a tin paint into one end of the reactor, draining the excess, pouring the tin paint into the other end of the reactor, draining the excess, and then reducing the tin paint coating at approximately 1050° F. for approximately 40 hours. The tin paint used for, coating the reactor was prepared by mixing together by weight 7 parts Tin Ten Cem (Mooney Chemical, Co.), 6 parts isopropyl alcohol, 14 parts tin powder (1–5 microns) and 14 parts stannic oxide (−325 mesh) and 5% $Fe_2O_3$ in paint mixture. Toluene at 24 μl/min was fed into the reactor with nitrogen at 20 cc/min for approximately 596 hours of operation at 1400° F. No plugging occurred but operational problems in letdown system caused shutdown.

EXAMPLE 2

A thermal hydrodealkylation reactor was prepared as described in Example 1 except that no $Fe_2O_3$ was used in the paint. Into the reactor which was maintained at 1250° F. and 100 psig, toluene at 25 μl/min and hydrogen at 20 cc/mm were introduced for approximately 88 hours of operation. Then, the temperature was raised to 1400° F. The reaction was continued until approximately 303 hours of operation occurred. No plugging of the reactor occurred.

EXAMPLE 3

Figure 2:
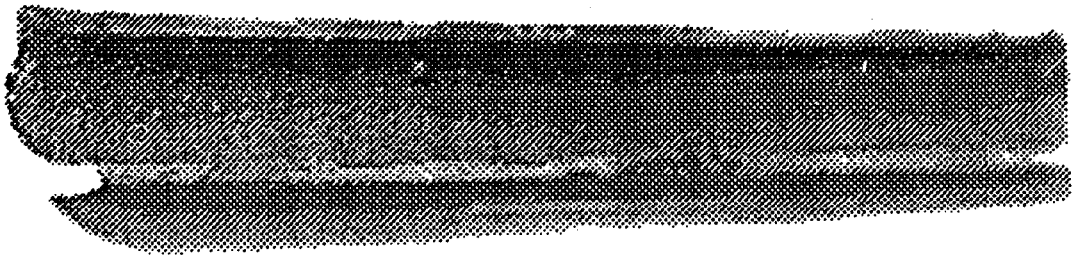
FIG. 2 is a photograph of a thermal hydrodealkylation reactor of the present invention which did not plug during operation.

A thermal hydrodealkylation reactor was prepared as described in Example 1. The reactor was preheated and maintained at a temperature of 1400° F. Toluene at 25 μl/min was fed into the reactor with hydrogen at 10 cc/min. The reactor pressure was maintained at approximately 100 psig. The reaction was allowed to proceed for at least 597 hours before changing the feed to n-hexane. No plugging of the reactor occurred during approximately 600 hours of operation. See FIG. 2 which is a photograph of the reactor cut open to show that no plugging occurred.

EXAMPLE 4

A thermal hydrodealkylation reactor was prepared as described in Example 2. The reactor was preheated and maintained at 1400° F. Toluene containing 50 ppm $CS_2$ at 25 μl/min was fed into the reactor with hydrogen at 10 cc/min. The reaction pressure was maintained at approximately 100 psig. After approximately 44 hours of operation, the amount of $CS_2$ in the toluene feed was reduced to 5 ppm. After approximately 719 hours of operation, the amount of $CS_2$ in the toluene feed, was reduced to 0.5 ppm. The reactor was not plugged upon reading approximately 1079 hours of operation but plugged upon reading approximately 1219 hours of operation due to an operational problem in the letdown system.

EXAMPLE 5

A thermal hydrodealkylation reactor was prepared as described in Example 2. The reactor was preheated and maintained at approximately 1400° F. Toluene containing 50 ppm $CS_2$ at 25 μl/min was fed into the reactor with hydrogen of 10 cc/min. The reactor pressure was maintained at approximately 100 psig. The reactor was shut down upon reaching approximately 695 hours of operation. No plugging occurred.

While the invention has been described above in terms of preferred embodiments, it is to be understood that variations and modifications may be used as will be appreciated by those skilled in the art. Essentially, therefore, there are many variations and modifications to the above preferred embodiments which will be readily evident to those skilled in the art and which are to be considered within the scope of the invention as defined by the following claims.

What is claimed is:

1. A method for hydrodealkylating a hydrodealkylatable hydrocarbon comprising (i) treating at least a portion of a hydrodealkylation reactor system with a carburization resistant composition, and (ii) contacting said hydrocarbon in said treated reactor system with hydrogen under low sulfur hydrodealkylation conditions of 100 ppm or less *and wherein said carburization resistant composition comprises, in major proportion, a member selected from the group consisting of aluminum, antimony, arsenic, bismuth, brass, gallium, germanium, indium, lead, selenium, tellurium, tin or intermetallic compounds and alloys thereof.*

2. The method for hydrodealkylating a hydrodealkylatable hydrocarbon according to claim 1, wherein treating step (i) comprises applying a coating or film of a carburization resistant composition to a surface of the reactor system susceptible to carburization under hydrodealkylation conditions.

[3. The method for hydrodealkylating a hydrodealkylatable hydrocarbon according to claim 2, wherein said carburization resistant composition comprises a member selected from the group consisting of aluminum, antimony, arsenic, bismuth, brass, chromium, copper, germanium, indium, lead, selenium, tellurium, tin or intermetallic compounds and alloys thereof.]

4. The method for hydrodealkylating a hydrodealkylatable hydrocarbon according to claim [3] *1*, wherein at least a portion of said coating or film is a Cu—Sn alloy or a Cu—Sb alloy.

5. The method for hydrodealkylating a hydrodealkylatable hydrocarbon according to claim 2, wherein said coating or film is provided as a plating, cladding, paint or other coating, to a base construction material.

6. The method for hydrodealkylating a hydrodealkylatable hydrocarbon according to claim 1, wherein said carburization resistant composition contains tin.

7. A method for hydrodealkylating a hydrodealkylatable hydrocarbon according to claim 1, comprising adding an anti-carburizing and anti-coking agent selected from the group of organo-tin compounds, organo-antimony compounds, organo-bismuth compounds, organo-arsenic compounds and organo-lead compounds to the hydrocarbon.

8. The method for hydrodealkylating a hydrodealkylatable hydrocarbon according to claim 1, wherein an organo-tin non-sulfur, anti-carburizing and anti-coking agent is added to the hydrocarbon.

9. The method for hydrodealkylating a hydrodealkylatable hydrocarbon according to claim 1, wherein at least a portion of said reactor system is constructed from a *nickel containing stainless* steel [having sufficient chromium content] so that an intermediate layer comprising chromium and carbide between the steel and an outer protective layer is formed when the steel is treated with a metal coating resistant to carburization comprising tin, antimony, bismuth or arsenic.

10. The method of claim 9, wherein the metal coating comprises tin.

11. The method of claim 10, wherein the tin coating is applied by electroplating, vapor deposition or soaking in a molten tin bath.

12. The method for hydrodealkylating a hydrodealkylatable hydrocarbon according to claim 1, wherein said portion of the reactor system is made of steel and treated by coating with aluminum or tin followed by application of a chromium oxide coating having a thickness sufficient to protect the aluminum coated or tin coated steel from carburization, metal-dusting and coking under low sulfur reaction conditions.

13. The method according to claim 12, wherein said portion of the reactor system has been coated with aluminum by deeply diffusing a mixture of blended aluminum powders onto said portion at elevated temperatures.

14. The method according to claim 12, wherein said portion of the reactor system has been coated with tin by electroplating.

15. The method for hydrodealkylating a hydrodealkylatable hydrocarbon according to claim 1, wherein a portion of said reactor system has initially been coated with a coating comprising aluminum, followed by a post-treatment process comprising application of a metal coating comprising tin.

16. The method according to claim 15, wherein the initial aluminum coating is applied by deeply diffusing a mixture of blended aluminum powders onto said portion at elevated temperatures.

17. The method for hydrodealkylating a hydrodealkylatable hydrocarbon according to claim 1, wherein a portion of said reactor system is exposed to temperatures of at least about 700° F. during said contacting.

18. The method for hydrodealkylating a hydrodealkylatable hydrocarbon according to claim 16, wherein a portion of said reactor system is exposed to temperatures of at least about 900° F. during said contacting.

19. The method for hydrodealkylating a hydrodealkylatable hydrocarbon according to claim 18, wherein a portion of said reactor system is exposed to temperatures of between about 900° F. and 1800° F. during said contacting.

20. The method for hydrodealkylating a hydrodealkylatable hydrocarbon according to claim 1, wherein said contacting takes place in the absence of a catalyst.

21. The method for hydrodealkylating a hydrodealkylatable hydrocarbon according to claim 1, wherein said hydrocarbon comprises an alkyl-substituted benzene.

22. The method for hydrodealkylating a hydrodealkylatable hydrocarbon according to claim 21, wherein said hydrocarbon is selected from the group consisting of toluene, m-xylene, o-xylene, p-xylene, mixed xylenes, ethyl benzene, n-propyl benzene, n-butyl benzene, cumene, isobutylbenzene, sec-butylbenzene, tert butylbenzene, and p-cymene.

23. The method for hydrodealkylating a hydrodealkylatable hydrocarbon according to claim 22, wherein said hydrocarbon is toluene.

24. The method for hydrodealkylating a hydrodealkylatable hydrocarbon according to claim 1, wherein toluene is contacted with hydrogen at a temperature from about 900° F. to 1800° F.

25. The method of hydrodealkylating a hydrodealkylatable hydrocarbon according to claim 24, wherein said portion of said reactor system is coated with a film of a carburization resistant composition comprising tin or antimony.

26. A method according to claim 1, wherein sulfur levels in the reactor system do not exceed about 50 ppm.

27. A method according to claim 26, wherein sulfur levels in the reactor system do not exceed about 20 ppm.

28. A method for hydrodealkylating a hydrodealkylatable hydrocarbon comprising:

(i) providing a carburization and abrasion resistant protective layer to a *nickel containing stainless* steel portion of a hydrodealkylation reactor system by (a) applying to the *stainless* steel portion a metal plating, cladding or other coating of a metal effective for forming a carburization resistant protective layer, to a thickness effective to isolate the steel portion from hydrocarbons during operation while avoiding any substantial liquid metal embrittlement, and (b) forming the protective layer, anchored to the *stainless* steel portion through an intermediate bonding layer comprising carbide;

(ii) hydrodealkylating a hydrodealkylatable hydrocarbon feed wherein the sulfur levels in the reactor system do not exceed 100 ppm *and wherein said metal is applied as a plating, cladding, or other coating comprising at least in major portion a metal selected from the group consisting of antimony, arsenic, bismuth, aluminum, gallium, germanium, indium, lead, selenium, tellurium, tin and mixtures thereof.*

29. A method for hydrodealkylating a hydrodealkylatable hydrocarbon according to claim 28, wherein said hydrocarbon feed comprises an alkyl-substituted benzene.

30. A method for hydrodealkylating a hydrodealkylatable hydrocarbon according to claim 28, wherein said hydrocarbon feed comprises at least one member selected from the group consisting of toluene, m-xylene, o-xylene, p-xylene, mixed xylenes, ethyl benzene, n-propyl benzene, n-butyl benzene, cumene, isobutyl benzene, sec-butyl benzene, tert butyl benzene, and p-cymene.

31. A method for hydrodealkylating a hydrodealkylatable hydrocarbon according to claim 30, wherein said hydrocarbon feed comprises toluene.

32. A method for hydrodealkylating a hydrodealkylatable hydrocarbon according to claim 28, wherein toluene is contacted with hydrogen under temperature conditions of from about 900° F. to 1800° F.

33. A method according to claim 28, wherein sulfur levels do not exceed about 50 ppm.

34. A method according to claim 33, wherein sulfur levels do not exceed about 20 ppm.

[35. A method according to claim 28, wherein the metal is applied as a plating, cladding or other coating comprising at least in major proportion selected from the group consisting of antimony, arsenic, bismuth aluminum, copper, chromium, gallium, germanium, indium, lead, selenium, tellurium, tin and mixtures thereof.]

36. A method according to claim [35] *28*, wherein the material is selected from tin, antimony, germanium, selenium, *and* tellurium [and chromium].

37. A method according to claim 36, wherein the material is selected from tin, antimony, *and* germanium [and chromium].

38. A method according to claim [35] *28*, wherein the metal plating, cladding or other coating is applied to a thickness of between 0.5 mils and 15 mils.

39. A method according to claim 38, wherein the metal plating, cladding or other coating is applied to a thickness of between 1 and 10 mils.

40. A method,according to claim 39, wherein the metal plating, cladding or other coating is applied to a thickness of between 2 and 8 mils.

41. A method according to claim 28, wherein the protective layer is applied to a furnace tube.

42. A method according to claim [35] *28*, wherein the metal is applied as a plating.

43. A method according to claim [35] *28*, wherein the metal is applied as a paint.

44. A method according to claim 43, wherein the metal is applied as a tin-containing paint.

45. A method according to claim 44, wherein the metal is applied as a tin-containing paint comprising a hydrogen decomposable tin compound, a solvent system, a finely divided tin metal and tin oxide effective as a sponge/dispersing/binding agent.

46. A method according to claim 44, wherein the paint contains iron.

47. A method according to claim 46, wherein the paint contains tin to iron in a ratio of between 10 and 1 by weight.

[48. A method according to claim 28, wherein the steel portion is a stainless steel portion and the bonding layer comprises carbide.]

49. A method according to claim 28, further comprising forming at least one additional protective layer on the surface of the protective layer.

50. A method according to claim 49, further comprising forming a copper-based protective layer on a stannide protective layer.

51. A hydrocarbon conversion process conducted with a hydrocarbon feed having a sulfur content lower than about 100 ppm, said process selected from the group consisting of nonoxidative dehydrogenation of hydrocarbons to olefins and dienes, oxidative dehydrogenation of hydrocarbons to olefins and dienes, dehydrogenation of ethylbenzene to styrene, conversion of light hydrocarbons to aromatics, transalkylation of toluene to benzene and xylenes, dealkylation of alkylaromatics to aromatics, alkylation of aromatics to alkylaromatics, production of fuels and chemicals from $H_2$ and CO, steam reforming of hydrocarbons to $H_2$ and CO, and methanol alkylation of toluene to xylenes, comprising:

(i) providing a carburization and abrasion resistant protective layer to a *nickel containing stainless* steel portion of a reactor system by (a) applying to the *stainless* steel portion a metal plating, cladding or other coating of a metal effective for forming a carburization resistant protective layer, to a thickness effective to isolate the steel portion from hydrocarbons during operation while avoiding any substantial liquid metal embrittlement, and (b) forming the protective layer, anchored to the *stainless* steel portion through an intermediate carbide-rich bonding layer comprising carbide;

(ii) converting hydrocarbons in the reactor system *and wherein said metal is applied as a plating, cladding or other coating comprising at least in major proportion a metal selected from the group consisting of antimony, arsenic, bismuth, aluminum, gallium, germanium, indium, lead, selenium, tellurium, tin and mixtures thereof.*

[52. A low-sulfur hydrocarbon conversion process according to claim 51, wherein the metal is applied as a plating, cladding or other coating comprising at least one metal in major proportion selected from the group consisting of antimony, arsenic, bismuth aluminum, copper, chromium, gallium, germanium, indium, lead, selenium, tellurium, tin and mixtures thereof.]

53. A method according to claim [52] *51*, wherein the metal plating, cladding or other coating is applied to a thickness of between 0.5 mils and 15 mils.

54. A method according to claim 53, wherein the metal plating, cladding or other coating is applied to a thickness of between 1 and 10 mils.

55. A method according to claim 54, wherein the metal plating, cladding or other coating is applied to a thickness of between 2 and 8 mils.

56. A method according to claim 53, wherein the protective layer is applied to a furnace tube.

57. A method according to claim [52] *51*, wherein the metal is applied as a plating.

[58. A method according to claim 57, wherein the metal is applied as a chromium plating.]

59. A method according to claim [52] *51*, wherein the metal is applied as a paint.

60. A method according to claim 59, wherein the metal is applied as a tin-containing paint.

61. A method according to claim 60, wherein the metal is applied as a tin-coating paint comprising a hydrogen decomposable tin compound, a solvent system, a finely divided tin metal and tin oxide effective as a sponge/dispersing/binding agent.

62. A method according to claim 60, wherein the paint contains iron.

63. A method according to claim 62, wherein the paint contains tin to iron in a ratio of between 10 and 1 by weight.

[64. A method according to claim 59, wherein the metal is applied as a chromium-containing paint.]

[65. A method according to claim 52, wherein the steel portion is a stainless steel portion and the bonding layer comprises carbide.]

66. A method according to claim [52] *51*, wherein the metal is selected from tin, antimony, germanium, selenium, tellurium, [chromium,] and mixtures thereof.

67. A method according to claim 66, wherein the metal is selected from tin, antimony, germanium, [chromium,] and mixtures thereof.

68. A process according to claim 51, wherein said low-sulfur hydrocarbon conversion process is selected from the conversion of $C_2$–$C_5$ hydrocarbons to aromatics, production of fuels and chemicals from $H_2$ and CO, and steam reforming of hydrocarbons to $H_2$ and CO.

*69. In a method for hydrodealkylating and hydrodealkylatable hydrocarbon wherein said hydrocarbon is contacted with hydrogen the improvement comprising conducting said hydrodealkylation under low sulfur hydrodealkylation conditions of 100 ppm or less in a reactor system in which at least a portion of said reactor system which is susceptible to carburization has been subjected to treatment with a carburization resistant composition wherein said treatment comprises applying a coating or film of said carburization resistant composition and wherein said composition comprises, in major proportion, a member selected from the group consisting of aluminum, antimony, arsenic, bismuth, brass, germanium, indium, lead, selenium, tellurium, tin or intermetallic compounds and alloys thereof.*

*70. The method of claim 69, wherein at least a portion of said coating or film is a Cu—Sn alloy or a Cu—Sb alloy.*

*71. The method of claim 69, wherein said treatment is applied as a coating or film provided as a plating, cladding, paint or other coating, to a base construction material.*

*72. The method of claim 69, wherein said carburization resistant composition contains tin.*

*73. The method of claim 69, wherein said treatment is effected by adding an anti-carburizing and anti-coking agent selected from the group of organo-tin compounds, organo-antimony compounds, organo-bismuth compounds, organo-arsenic compounds and organo-lead compounds to said hydrocarbon.*

*74. The method to claim 69, wherein said treatment is effected by adding an organo-tin non-sulfur, anti-carburizing and anti-coking agent to the hydrocarbon.*

*75. The method of claim 69, wherein at least a portion of said reactor system is constructed from a stainless steel treated with a metal coating resistant to carburization comprising tin, antimony, germanium, bismuth or arsenic.*

*76. The method of claim 75, wherein said coating comprises tin.*

*77. The method of claim 76, wherein the tin coating is applied by electroplating, vapor deposition, or soaking in a molten tin bath.*

*78. The method of claim 69, wherein said portion of the reactor system is made of steel and wherein said treatment comprises coating said portion with aluminum or tin followed by application of a chromium oxide coating having a thickness sufficient to protect the aluminum coated or tin coated steel from carburization, metal-dusting and coking under low sulfur reaction conditions.*

*79. The method of claim 78, wherein said portion of the reactor system has been coated with aluminum by deeply diffusing a mixture of blended aluminum powders onto said portion at elevated temperatures.*

*80. The method according to claim 78, wherein said portion of the reactor system has been coated with tin by electroplating.*

*81. The method of claim 69, wherein a portion of said reactor system has initially been coated with a coating comprising aluminum, followed by a post-treatment process comprising application of a metal coating comprising tin.*

*82. The method of claim 69, wherein a portion of said reactor system is exposed to temperatures of at least about 700° F. during said contacting.*

*83. The method of claim 82, wherein a portion of said reactor system is exposed to temperatures of between about 900° F. and 1800° F. during said contacting.*

*84. The method of claim 69, wherein said contacting takes place in the absence of a catalyst.*

*85. The method of claim 69, wherein said hydrocarbon comprises an alkyl-substituted benzene.*

*86. The method of claim 85, wherein said hydrocarbon is selected from the group consisting of toluene, m-xylene, o-xylene, p-xylene, mixed xylenes, ethyl benzene, n-propyl benzene, n-butyl benzene, cumene, isobutylbenzene, sec-butylbenzene, tert butylbenzene, and p-cymene.*

*87. The method of claim 85, wherein said hydrocarbon is toluene.*

*88. The method of claim 87, wherein said portion of said reactor system is coated with a film of a carburization resistant composition comprising tin or antimony.*

*89. In a method for hydrodealkylating a hydrodealkylatable hydrocarbon the improvement comprising:*

*(i) conducting said method in a hydrodealkylation reactor system to which a nickel containing stainless steel portion of said reactor system has been provided with a carburization and abrasion resistant protective layer by (a) applying to said stainless steel portion a metal plating, cladding or other coating of a metal effective for forming a carburization resistant protective layer, to a thickness effective to isolate said stainless steel portion from hydrocarbons during operation while avoiding any substantial liquid metal embrittlement, and (b) forming the protective layer, anchored to said stainless the steel portion through an intermediate bonding layer comprising carbide; and*

*(ii) hydrodealkylating a hydrodealkylatable hydrocarbon feed wherein the sulfur levels in the reactor system do not exceed about 100 ppm; and wherein said metal was applied as a plating, cladding or other coating comprising at least in major proportion a metal selected from the group consisting of antimony, arsenic, bismuth, aluminum, gallium, germanium, indium, lead, selenium, tellurium, tin and mixtures thereof.*

*90. A method for hydrodealkylating a hydrodealkylatable hydrocarbon according to claim 89, wherein said hydrodealkylatable hydrocarbon comprises an alkyl-substituted benzene.*

*91. A method for hydrodealkylating a hydrodealkylatable hydrocarbon according to claim 89, wherein said hydrodealkylatable hydrocarbon comprises at least one member selected from the group consisting of toluene, m-xylene, o-xylene, p-xylene, mixed xylenes, ethyl benzene, n-propyl benzene, n-butyl benzene, cumene, isobutyl benzene, sec-butyl benzene, tert butyl benzene, and p-cymene.*

*92. A method for hydrodealkylating a hydrodealkylatable hydrocarbon according to claim 89, wherein toluene is contacted with hydrogen under temperature conditions of from about 900° F. to 1800° F.*

*93. The method of claim 89, wherein at least one additional protective layer has been formed on the surface of the protective layer.*

*94. The method of claim 93, wherein said additional layer is a copper-based protective layer and said protective layer is a stannide protective layer.*

*95. In a hydrocarbon conversion method selected from the group consisting of nonoxidative dehydrogenation of hydrocarbons to olefins and dienes; oxidative dehydrogenation of hydrocarbons to olefins and dienes; dehydrogenation of ethylbenzene to styrene; conversion of light hydrocarbons to aromatics; transalkylation of toluene to benzene and xylenes; dealkylation of alkylaromatics to aromatics; alkylation of aromatics to alkylaromatics; production of fuels and chemicals from $H_2$ and CO; steam reforming of hydrocarbons to $H_2$ and CO; and methanol alkylation of toluene to xylenes the improvement comprising conducting said hydrocarbon conversion with a hydrocarbon stream or $H_2$ and CO stream having a sulfur content lower than about 100 ppm in a reactor system in which a nickel containing stainless steel portion thereof has a carburization and abrasion resistant protective layer obtained by applying to said stainless steel portion a metal plating, cladding or other coating of a metal effective for forming a carburization resistant protective layer to thickness effective to isolate said stainless steel portion through an intermediate carbide-rich bonding layer comprising carbide and wherein said protective layer is formed from a plating, cladding or other coating comprising at least one metal in major proportion selected from the group consisting of antimony, arsenic, bismuth, aluminum, gallium, germanium, indium, lead, selenium, tellurium, tin and mixtures thereof.*

*96. The method of claim 95, wherein said hydrocarbon conversion process is selected from the conversion of $C_2$–$C_5$ hydrocarbons to aromatics; production of fuels and chemicals from $H_2$* and CO; and steam reforming hydrocarbons to $H_2$ *and CO.*

*97. The method of claim 96, wherein said hydrocarbon conversion process is the production of fuels and chemicals from $H_2$ and CO.*

*98. The method of claim 96, wherein said conversion process is steam reforming of hydrocarbons to $H_2$ and CO.*

*99. The method of claim 96, wherein said stainless steel portion comprises furnace tubes.*

*100. The method of claim 95, wherein said conversion process is selected from the group consisting of nonoxidative dehydrogenation of hydrocarbons to olefins and dienes and oxidative dehydrogenation of hydrocarbons to olefins and dienes.*

*101. The method of claim 95, wherein said conversion process is selected from the group consisting of dehydrogenation of ethylbenzene to styrene and the conversion of light hydrocarbons to aromatics.*

*102. The method of claim 95, wherein said conversion process is selected from the group consisting of the transalkylation of toluene to benzene and xylenes.*

*103. The method of claim 95, wherein said conversion process is selected from the group consisting of the alkylation of aromatics to alkylaromatics and the methanol alkylation of toluene to xylenes.*

*104. In a hydrocarbon conversion method selected from the group consisting of nonoxidative dehydrogenation of hydrocarbons to olefins and dienes; oxidative dehydrogenation of hydrocarbons to olefins and dienes; dehydrogenation of ethylbenzene to styrene; conversion of light hydrocarbons to aromatics; transalkylation of toluene to benzene and xylenes; dealkylation of alkylaromatics to aromatics; alkylation of aromatics to alkylaromatics; production of fuels and chemicals from $H_2$ and CO; steam reforming of hydrocarbons to $H_2$ and CO; and methanol alkylation of toluene to xylenes the improvement comprising conducting said hydrocarbon conversion with a hydrocarbon stream or $H_2$ and CO stream having a sulfur content lower than about 100 ppm in a reactor system in which an essentially nickel free steel portion thereof has a carburization and abrasion resistant protective layer obtained by applying to said steel portion a metal plating, cladding or other coating of a metal effective for forming a carburization resistant protective layer to thickness effective to isolate said steel portion from hydrocarbons during operation while avoiding any substantial liquid metal embrittlement and wherein said protective layer comprises intermetallic compounds or alloys of iron and said metal.*

*105. The method of claim 104, wherein said protective layer is formed from a plating, cladding or other coating comprising at least one metal in major proportion selected from the group consisting of antimony, arsenic, aluminum, copper, chromium, gallium, germanium, selenium, tellurium, tin and mixtures thereof.*

*106. The method of claim 104, wherein said hydrocarbon conversion process is selected from the conversion of $C_2$–$C_5$ hydrocarbons to aromatics, production of fuels and chemicals from $H_2$ and CO, and steam reforming hydrocarbons to $H_2$ and CO.*

*107. The method of claim 106, wherein said hydrocarbon conversion process is the production of fuels and chemicals from $H_2$ and CO.*

*108. The method of claim 107, wherein said protective layer is formed from a plating, cladding or other coating comprising at least one metal in major proportion selected from the group consisting of antimony, arsenic, aluminum, copper, chromium, gallium, germanium, selenium, tellurium, tin and mixtures thereof.*

*109. The method of claim 104, wherein said conversion process is steam reforming of hydrocarbons to $H_2$ and CO.*

*110. The method of claim 109, wherein the protective layer is formed from a plating, cladding or other coating comprising at least one metal in major proportion selected from the group consisting of antimony, arsenic, aluminum, copper, chromium, gallium, germanium, selenium, tellurium, tin and mixtures thereof.*

*111. The method of claim 106, wherein said steel portion comprises furnace tubes.*

*112. The method of claim 104, wherein said conversion process is selected from the group consisting of nonoxidative dehydrogenation of hydrocarbons to olefins and dienes and oxidative dehydrogenation of hydrocarbons to olefins and dienes.*

*113. The processing according to claim 112, wherein said protective layer is formed from a plating, cladding or other coating comprising at least one metal in major proportion selected from the group consisting of antimony, arsenic, aluminum, copper, chromium, gallium, germanium, selenium, tellurium, tin and mixtures thereof.*

*114. The method of claim 104, wherein said conversion process is selected from the group consisting of dehydrogenation of ethylbenzene to styrene and the conversion of light hydrocarbons to aromatics.*

*115. The processing according of claim 114, wherein said protective layer is formed from a plating, cladding or other coating comprising at least one metal in major proportion selected from the group consisting of antimony, arsenic, bismuth, aluminum, copper, chromium, gallium, germanium, indium, lead, selenium, tellurium, tin and mixtures thereof.*

*116. The method of claim 104, wherein said conversion process is selected from the group consisting of the transalkylation of toluene to benzene and xylenes.*

*117. The method according to claim 116, wherein said protective layer is formed from a plating, cladding or other coating comprising at least one metal in major proportion selected from the group consisting of antimony, arsenic, bismuth, aluminum, copper, chromium, gallium, germanium, indium, lead, selenium, tellurium, tin and mixtures thereof.*

*118. The method of claim 104, wherein said conversion process is selected from the group consisting of the alkylation of aromatics to alkylaromatics and the methanol alkylation of toluene to xylenes.*

*119. The method according to claim 118, wherein said protective layer is formed from a plating, cladding or other coating comprising at least one metal in major proportion selected from the group consisting of antimony, arsenic, aluminum, copper, chromium, gallium, germanium, selenium, tellurium, tin and mixtures thereof.*

*120. The process of claim 104, wherein said steel is mild steel.*

*121. In a hydrocarbon conversion process selected from the group consisting of nonoxidative dehydrogenation of hydrocarbons to olefins and dienes; oxidative dehydrogenation of hydrocarbons to olefins and dienes; dehydrogenation of ethylbenzene to styrene; conversion of light hydrocarbons to aromatics; transalkylation of toluene to benzene and xylenes; dealkylation of alkylaromatics to aromatics; alkylation of aromatics to alkylaromatics; production of fuels and chemicals from $H_2$ and CO; steam reforming of hydrocarbons to $H_2$ and CO; and methanol alkylation of toluene to xylenes the improvement comprising conducting said hydrocarbon conversion with a hydrocarbon stream having a sulfur content lower than about 100 ppm in a reactor system in which a steel portion thereof has a carburization and abrasion protective layer derived from a metal, in major proportion, selected from the group consisting of tin, arsenic, antimony, aluminum, bismuth, germanium, gallium, indium, selenium, tellurium, lead, brass and intermetallic compounds and alloys thereof attached thereto of a thickness effective to isolate the steel portion from hydrocarbons during operations while avoiding any substantial liquid embrittlement.*

*122. The process of claim 121, wherein said steel portion is nickel containing stainless steel and wherein said protective layer is anchored to said stainless steel portion thereof through an intermediate bonding layer comprising carbide and wherein said metal is selected from the group consisting of copper, tin, arsenic, germanium, gallium, selenium, tellurium and intermetallic compounds and alloys thereof.*

*123. The process of claim 121, wherein said steel portion is essentially nickel free steel and wherein said protective layer comprises at least one intermetallic compound or alloy of said metal and iron.*

*124. In a hydrocarbon conversion method utilizing a cracking furnace the improvement comprising conducting said hydrocarbon conversion with a hydrocarbon stream having a sulfur content lower than about 100 ppm and wherein a nickel containing stainless steel portion of said cracking furnace has a carburization and abrasion resistant protective layer obtained by applying to said stainless steel portion a metal plating, cladding or other coating of a metal effective for forming a carburization resistance protective layer of a thickness effective to isolate the steel portion from hydrocarbons during operation while avoiding any substantial liquid metal embrittlement and wherein said protective layer is anchored to the stainless steel portion through an intermediate carbide-rich bonding layer comprising carbide and wherein said protective layer is formed from a plating, cladding or other coating comprising at least one metal in major proportion selected from the group consisting of antimony, arsenic, bismuth, aluminum, gallium, germanium, indium, lead, selenium, tellurium, tin and mixtures thereof.*

*125. The method of claim 124, wherein said hydrocarbon comprises ethane and said cracking furnace is an ethane cracking furnace having furnace tubes having said protective layer.*

*126. The method according to claim 125, wherein said metal coating is a plating, cladding or other coating comprising at least one metal in major proportion selected from the group consisting of antimony, arsenic, bismuth, aluminum, copper, gallium, germanium, indium, lead, selenium, tellurium, tin and mixtures thereof.*

*127. The process of claim 124, wherein said cracking furnace is operated at temperatures between 800 and 2000° F.*

*128. The process of claim 124, wherein said cracking furnace is operated at temperatures between 1400 and 1700° F.*

*129. The process of claim 124, wherein said hydrocarbon is propane.*

*130. In a hydrocarbon conversion process utilizing a cracking furnace the improvement comprising conducting said hydrocarbon conversion with a hydrocarbon stream having a sulfur content lower than about 100 ppm and wherein an essentially nickel free steel portion of said cracking furnace has a carburization and abrasion resistant*

*protective layer obtained by applying to said steel portion a metal plating, cladding or other coating of a metal effective for forming a carburization resistent protective layer of a thickness effective to isolate the steel portion form hydrocarbons during operation while avoiding any substantial liquid metal embrittlement and wherein said protective layer comprises intermetallic compounds of or alloys of iron and said metal.*

*131. The process of claim 130, wherein said hydrocarbon is ethane.*

*132. The process of claim 130, wherein said hydrocarbon is propane.*

*133. The process of claim 130, wherein said steel is mild steel.*

*134. The method of claims 88, 89, 97, 121, 124 or 130 wherein said sulfur levels do not exceed 50 ppm.*

*135. The method of claims 88, 89, 97, 121, 124 or 130 wherein said sulfur levels do not exceed 20 ppm.*

*136. The method of claims 89, 95, 97, 98, 104, 107, 109, 124, or 127, wherein the plating, cladding or other coating has a thickness of between 0.5 mils and 15 mils.*

*137. The method of claims 89, 95, 97, 98, 104, 107, or 109 wherein the plating, cladding or other coating has a thickness of between 1 and 10 mils.*

*138. The method of claims 89, 95, 97, 98, 104, 107, 109, 124, or 130 wherein the plating, cladding or other coating has a thickness of between 2 and 8 mils.*

*139. The method of claims 89, 95, 97, 98, 104, 107, 109, 121, 124, or 130 wherein the metal is applied as a tin-containing paint.*

*140. The method of claims 89, 95, 97, 98, 104, 107, 109, 121, 127, or 130 wherein the metal is applied as a tin-containing paint comprising a hydrogen decomposable tin compound, a solvent system, a finely divided tin metal and tin oxide effective as a sponge/dispersing/binding agent.*

*141. The method of claim 140, wherein the paint contain iron.*

*142. The method of claim 141, wherein the paint contains iron in a tin to iron ratio of between 10 and 1 by weight.*

*143. The method of claim 95, 97, 98, 100, 101, 102, 103, 104, 106, 109, 112, 114, 116, 118, 124, 126, or 130 wherein a major portion of said plating, cladding or other coating is tin.*

*144. The method of claims 105, 108, 110, 113, 115, 117, 119, or 130, wherein a major portion of said plating, cladding or other coating is chromium.*

*145. A method according to claim 95, 97, 98, 100, 101, 102, 103, 104, 106, 109, 112, 114, 116, 118, 124, or 130 wherein the metal is selected from tin, antimony, germanium, selenium, tellurium, and mixtures thereof.*

*146. A method according to claim 145, wherein said metal is selected from tin, antimony, germanium, and mixtures thereof.*

*147. The method of claim 89, 97, 98, 104, 107, 109, 124, or 130 wherein the plating, cladding or other coating is a plating.*

*148. The method of claims 104, 108, 110, or 130, wherein the plating, cladding, or other coating is a plating and said plating is chromium plating.*

*149. The method of claim 89, 97, 98, 104, 107, or 109, wherein the plating, cladding or other coating is a paint.*

*150. The method of claims 105, 109, 110, or 130, wherein the plating, cladding or other coating is a paint and said paint is a chromium containing paint.*

*151. The method of claim 9, 51, or 89 wherein said nickel containing stainless steel contains about 75 wt. % nickel, 16 wt. % chromium and 9 wt. % iron.*

* * * * *